(12) United States Patent
Meltzer et al.

(10) Patent No.: US 8,956,815 B2
(45) Date of Patent: Feb. 17, 2015

(54) INTERCALATION METHODS AND DEVICES

(71) Applicant: PathoGenetix, Inc., Woburn, MA (US)

(72) Inventors: Robert H. Meltzer, Chelmsford, MA (US); Joshua W. Griffis, Gardner, MA (US)

(73) Assignee: Toxic Report LLC, Watertown, MA (US)

( * ) Notice: Subject to any disclaimer, the term of this patent is extended or adjusted under 35 U.S.C. 154(b) by 0 days.

(21) Appl. No.: 13/865,505

(22) Filed: Apr. 18, 2013

(65) Prior Publication Data

US 2013/0295686 A1 Nov. 7, 2013

Related U.S. Application Data

(60) Provisional application No. 61/635,263, filed on Apr. 18, 2012, provisional application No. 61/784,061, filed on Mar. 14, 2013.

(51) Int. Cl.
*C12Q 1/68* (2006.01)
*C12M 1/34* (2006.01)
*G01N 33/58* (2006.01)
*G01N 1/30* (2006.01)

(52) U.S. Cl.
CPC ............. *G01N 33/582* (2013.01); *G01N 1/30* (2013.01); *C12Q 1/6811* (2013.01)
USPC ........................................ 435/6.1; 435/287.2

(58) Field of Classification Search
None
See application file for complete search history.

(56) References Cited

U.S. PATENT DOCUMENTS

| | | | |
|---|---|---|---|
| 6,210,896 B1 | 4/2001 | Chan |
| 6,263,286 B1 | 7/2001 | Gilmanshin et al. |
| 6,355,420 B1 | 3/2002 | Chan |
| 6,403,311 B1 | 6/2002 | Chan |
| 6,696,022 B1 | 2/2004 | Chan et al. |
| 6,762,059 B2 | 7/2004 | Chan et al. |
| 6,772,070 B2 | 8/2004 | Gilmanshin et al. |
| 6,790,671 B1 | 9/2004 | Austin et al. |
| 6,927,065 B2 | 8/2005 | Chan et al. |
| 7,262,859 B2 | 8/2007 | Larson et al. |
| 7,282,330 B2 | 10/2007 | Zhao et al. |
| 7,351,538 B2 | 4/2008 | Fuchs et al. |
| 7,371,520 B2 | 5/2008 | Zhao et al. |
| 7,402,422 B2 | 7/2008 | Fuchs et al. |
| 7,595,160 B2 | 9/2009 | White et al. |
| 7,888,011 B2 | 2/2011 | Nilsen et al. |
| 7,977,048 B2 | 7/2011 | Gilmanshin |
| 8,114,636 B2 | 2/2012 | Agnew et al. |
| 8,168,380 B2 | 5/2012 | Chan |
| 8,361,716 B2 | 1/2013 | Patil |
| 8,423,294 B2 | 4/2013 | Nadel et al. |
| 8,518,705 B2 | 8/2013 | Chan et al. |
| 8,685,708 B2 | 4/2014 | Harris et al. |
| 2002/0110818 A1 | 8/2002 | Chan |
| 2002/0187508 A1 | 12/2002 | Wong |
| 2002/0197639 A1 | 12/2002 | Shia et al. |
| 2003/0059822 A1 | 3/2003 | Chan et al. |
| 2003/0215864 A1 | 11/2003 | Gilmanshin et al. |
| 2003/0235854 A1 | 12/2003 | Chan et al. |
| 2004/0053399 A1 | 3/2004 | Gilmanshin |
| 2004/0166025 A1 | 8/2004 | Chan et al. |
| 2004/0214211 A1 | 10/2004 | Gilmanshin et al. |
| 2005/0042665 A1 | 2/2005 | Gilmanshin et al. |
| 2005/0112606 A1 | 5/2005 | Fuchs et al. |
| 2005/0112620 A1 | 5/2005 | Chan |
| 2005/0112671 A1 | 5/2005 | Maletta et al. |
| 2005/0123944 A1 | 6/2005 | Neely et al. |
| 2005/0123974 A1 | 6/2005 | Gilmanshin et al. |
| 2005/0142565 A1 | 6/2005 | Samper et al. |
| 2005/0142595 A1 | 6/2005 | Maletta et al. |
| 2005/0196790 A1 | 9/2005 | Rooke |
| 2005/0221408 A1 | 10/2005 | Nalefski et al. |
| 2006/0134679 A1 | 6/2006 | Larson |
| 2006/0160231 A1 | 7/2006 | Nadel et al. |
| 2006/0292616 A1 | 12/2006 | Neely et al. |
| 2006/0292617 A1 | 12/2006 | Neely et al. |
| 2007/0042406 A1 | 2/2007 | Yantz et al. |
| 2007/0128083 A1 | 6/2007 | Yantz et al. |
| 2007/0166743 A1 | 7/2007 | Gilmanshin |
| 2008/0003689 A1 | 1/2008 | Lee et al. |
| 2008/0085521 A1 | 4/2008 | Knapp et al. |
| 2008/0085552 A1 | 4/2008 | Larson et al. |
| 2008/0103296 A1 | 5/2008 | Zhao et al. |
| 2008/0254549 A1 | 10/2008 | Fuchs et al. |
| 2008/0280285 A1 | 11/2008 | Chen et al. |
| 2009/0035770 A1 | 2/2009 | Mathies et al. |
| 2010/0035247 A1 | 2/2010 | Burton et al. |
| 2010/0116025 A1 | 5/2010 | Gouveia et al. |

(Continued)

FOREIGN PATENT DOCUMENTS

WO WO 98/35012 A2 8/1998
WO WO 99/28500 A1 6/1999

(Continued)

OTHER PUBLICATIONS

Tan et al, J. Chromatography A 853: 309 (1999).*
Gibson et al, J. Cap. Elect. 5 (1 & 2), 73 (1998).*
Berge et al., Structural perturbations in DNA caused by bis-intercalation of ditercalinium visualised by atomic force microscopy. Nucleic Acids Res. Jul. 1, 2002;30(13):2980-6.
Burton et al., A microfluidic chip-compatible bioassay based on single-molecule detection with high sensitivity and multiplexing. Lab Chip. Apr. 7, 2010;10(7):843-51. doi: 10.1039/b922106a. Epub Jan. 14, 2010.
Carlsson et al., Double bands in DNA gel electrophoresis caused by bis-intercalating dyes. Nucleic Acids Res. Jul. 11, 1995;23(13):2413-20.

(Continued)

*Primary Examiner* — James Martinell
(74) *Attorney, Agent, or Firm* — Wolf, Greenfield & Sacks, P.C.

(57) ABSTRACT

The invention provides devices and methods for improving labeling of nucleic acids including intercalation of nucleic acids using for example mono intercalators such as mono cyanine intercalators.

21 Claims, 9 Drawing Sheets

(56) References Cited

U.S. PATENT DOCUMENTS

| | | | |
|---|---|---|---|
| 2010/0120101 | A1 | 5/2010 | Patil et al. |
| 2010/0234237 | A1 | 9/2010 | Yoo |
| 2010/0294665 | A1 | 11/2010 | Allen et al. |
| 2012/0283955 | A1 | 11/2012 | Cameron et al. |
| 2013/0000738 | A1 | 1/2013 | Krogmeier et al. |
| 2013/0266935 | A1 | 10/2013 | Patil |
| 2013/0288234 | A1 | 10/2013 | Harris et al. |
| 2013/0309780 | A1 | 11/2013 | Meltzer et al. |
| 2014/0011686 | A1 | 1/2014 | Gilmanshin |
| 2014/0135489 | A1 | 5/2014 | Harris et al. |
| 2014/0234985 | A9 | 8/2014 | Meltzer et al. |

FOREIGN PATENT DOCUMENTS

| | | | |
|---|---|---|---|
| WO | WO 01/46467 | A2 | 6/2001 |
| WO | WO 2005/078137 | A1 | 8/2005 |
| WO | WO 2005/085849 | A2 | 9/2005 |
| WO | WO 2008/024483 | A1 | 2/2008 |

OTHER PUBLICATIONS

Carlsson et al., Optical and photophysical properties of the oxazole yellow DNA probes YO and YOYO. J Phys Chem. 1994;98(40):10313-21.

Chan et al., DNA mapping using microfluidic stretching and single-molecule detection of fluorescent site-specific tags. Genome Res. Jun. 2004;14(6):1137-46.

Fürstenberg et al., Structure-fluorescence contrast relationship in cyanine DNA intercalators: toward rational dye design. Chemistry. 2007;13(30):8600-9.

Griffis et al., High-throughput genome scanning in constant tension fluidic funnels. Lab Chip. Jan. 21, 2013;13(2):240-51. doi: 10.1039/c2lc40943g. Epub Dec. 3, 2012. Supplemental Material Included. 8 pgs.

Günther et al., Mechanical and structural properties of YOYO-1 complexed DNA. Nucleic Acids Res. Oct. 2010;38(19):6526-32. doi:10.1093/nar/gkq434. Epub May 28, 2010.

Jung et al., On-chip millionfold sample stacking using transient isotachophoresis. Anal Chem. Apr. 1, 2006;78(7):2319-27.

Krylova et al., Transverse diffusion of laminar flow profiles—a generic method for mixing reactants in capillary microreactor. J Sep Sci. Mar. 2009;32(5-6):742-56. doi: 10.1002/jssc.200800671.

Kumar et al., Evaluation of genome sequence scanning technology for molecular (sub)-serotyping of *Salmonella* and simultaneous detection of multiple *Salmonella* serovars in complex mixtures. 4th Am Soc for Microbiol (ASM) Meeting on *Salmonella*. Oct. 9, 2013. Poster. 1 Page.

Kumar et al., Molecular serotyping and sub-typing of *Salmonella* strains by genome sequence scanning. Int'l Assoc for Food Protect Ann Mtg. Jul. 31, 2013. Poster. 1 Page.

Kumar et al., Molecular strain typing of Shiga-toxigenic *E. coli* (STEC) by genome sequence scanning. Assoc Pub Health Lab Gen Mtg. Jun. 2, 2013. 1 Page.

Kumar et al., Molecular strain typing of Shiga-toxigenic *E. coli* (STEC) by genome sequence scanning. Am Soc for Microbiol Gen mtg. May 20, 2013. Poster. 1 Page.

Larson et al., Single DNA molecule stretching in sudden mixed shear and elongational microflows. Lab Chip. Sep. 2006;6(9):1187-99. Epub Jul. 7, 2006.

Larsson et al., Characterization of the Binding of the Fluorescent Dyes YO and YOYO to DNA by Polarized Light Spectroscopy. Journal of the American Chemical Society. Sep. 1, 1994;116(19):8459-8465. doi:10.1021/ja00098a004.

Malkin et al., Rapid detection and sub-serotype level typing of bacterial organisms using optical genome sequence scanning. Am Soc Microbiol Gen Meeting. 2013. Poster. 1 Page.

Meltzer et al., A lab-on-chip for biothreat detection using single-molecule DNA mapping. Lab Chip. Mar. 7, 2011;11(5):863-73. Epub Jan. 20, 2011. Supplemental Material Included.

Mollova et al., An automated sample preparation system with mini-reactor to isolate and process submegabase fragments of bacterial DNA. Anal Biochem. Aug. 15, 2009;391(2):135-43. Epub May 12, 2009. Supplemental Material Included. 23 Pages.

Nirode et al., Evaluation of a sheath flow cuvette for postcolumn fluorescence derivatization of DNA fragments separated by capillary electrophoresis. Anal Chem. Jan. 1, 1998;70(1):182-6.

Phillips et al., Application of single molecule technology to rapidly map long DNA and study the confirmation of stretched DNA. Nuc Acids Res. 2005;33(18):5829-5837.

Pouseele et al., An Integrated Rapid Strain Typing Solution Combined With a Polyphasic Bioinformatics Tool has the Potential to Considerably Reduce the Time for Routine Outbreak Detection. InFORM 2013: Integrated Foodborne Outbreak Response and Management Meeting. Nov. 19, 2013. Poster. 1 Page.

Protozanova et al., Fast high-resolution mapping of long fragments of genomic DNA based on single-molecule detection. Anal Biochem. Jul. 1, 2010;402(1):83-90. Epub Mar. 20, 2010.

Protozanova et al., Fast high-resolution mapping of long fragments of genomic DNA based on single-molecule detection. Anal Biochem. Jul. 1, 2010;402(1):83-90. Epub Mar. 20, 2010. Supplemental Data. 29 Pages.

Ramaswamy et al., Confirmation and typing of *Salmonella* by genome sequence scanning in presumptive positive food samples. Pathogenex Poster. Jul. 30, 2013. 1 Page.

Ramaswamy et al., Rapid strain typing of *Salmonella* in food in the presence of competing microflora by genome sequence scanning. Am Soc Microbiol Gen Mtg. May 29, 2013. Poster. 1 Page.

Shackman et al., Gradient elution isotachophoresis for enrichment and separation of biomolecules. Anal Chem. Sep. 1, 2007;79(17):6641-9. Epub Aug. 4, 2007.

Swerdlow et al., Capillary gel electrophoresis for DNA sequencing. Laser-induced fluorescence detection with the sheath flow cuvette. J Chromatogr. Sep. 7, 1990;516(1):61-7.

White et al., *Staphylococcus aureus* strain typing by single-molecule DNA mapping in fluidic microchips with fluorescent tags. Clin Chem. Dec. 2009;55(12):2121-9. Epub Oct. 8, 2009.

White et al., *Staphylococcus aureus* strain typing by single-molecule DNA mapping in fluidic microchips with fluorescent tags. Clin Chem. Dec. 2009;55(12):2121-9. Epub Oct. 8, 2009. Supplemental Data.

Zhao et al., Use of a sheath flow cuvette for chemiluminescence detection of isoluminol thiocarbamyl-amino acids separated by capillary electrophoresis. J Microcol. Sep. 5, 1993;5:331-339.

[No Author Listed] Simultaneous DNA Stretching and Intercalation in Continuous Elongational Flow. 58th Annual Meeting of the Biophysical Society, San Francisco, CA. PathoGenetix Poster Abstract. Feb. 15-19, 2014. 1 Page.

Chan et al., DNA mapping technology based on microfluidic stretching and single-molecule detection of motif tags. Biophys J. 2003;84:302A. Poster 1470. Board #B725. 1 Page.

Cluzel et al., DNA: an extensible molecule. Science. Feb. 9, 1996;271(5250):792-4.

D'Antoni et al., Single Molecule Detection of Proteins Using Microfluidic Fluorescence Detection. ORC Poster. Apr. 2006. 1 Page.

Kumar et al., Strain typing of BIG 7 STECs and differentiation from stx- and/or eae-BIG 7 serogroup *E. coli* by Genome Sequence Scanning. 114th General Meeting American Society of Microbiology, May 19, 2014. Poster. 1 Page.

Meltzer et al., Multivariable Parameter Optimization of Microfluidic Post Arrays for DNA Fractionation. Biophysical Society 53rd Annual Meeting. Feb. 28-Mar. 4, 2009. Boston. Poster. 1 Page.

Protozanova et al., Rapid Molecular Serotyping of *Listeria* spp. by Genome Sequence Scanning. 114th General Meeting American Society of Microbiology, May 19, 2014. Poster. 1 Page.

Soslau et al., 1983 Selective inhibition of restriction endonuclease cleavage by DNA intercalators Biochem Biophys Res Commun 1983 115(2): 484-491.

Yamane, Smart probe: a novel fluorescence quenching-based oligonucleotide probe carrying a fluorophore and an intercalator. Nucleic Acids Symp Ser. 2000;(44):297-8.

\* cited by examiner

INTERCALATION METHODS AND DEVICES

RELATED APPLICATIONS

This application claims the benefit under 35 U.S.C. §119 (e) of U.S. Provisional Application Ser. No. 61/635,263, entitled "INTERCALATION METHODS AND DEVICES" filed on Apr. 18, 2012, and U.S. Provisional Application Ser. No. 61/784,061, entitled "INTERCALATION METHODS AND DEVICES" filed on Mar. 14, 2013, the entire contents of both of which are incorporated herein by reference.

BACKGROUND OF INVENTION

Non-specific backbone staining of nucleic acids with intercalating dyes is a fundamental requirement of certain nucleic acid manipulations and analyses. (Chan, Goncalves et al. 2004; Jung, Bharadwaj et al. 2006; Larson, Yantz et al. 2006; Shackman and Ross 2007; Protozanova, Zhang et al. 2010). As an example, in Direct Linear Analysis (DLA) or Genome Sequence Scanning (GSS™), backbone specific staining is used to determine presence, velocity and length of nucleic acids.

Typically, intercalation reactions are performed by adding an appropriate mass of a specific intercalating dye to a known mass of DNA, resulting in a fixed molar ratio of individual fluorophores to nucleic acid base pairs. However, variable starting cell load, genomic content, and DNA extraction efficiencies can cause the mass yields between sample preparations to be inconsistent. This can complicate analyses by requiring that nucleic acid mass be pre-quantified.

SUMMARY OF INVENTION

The invention provides various methods and related systems for uniformly labeling nucleic acids with, for example, backbone stains without knowledge of the amount (i.e., mass) and thus the concentration of nucleic acid being labeled. The invention contemplates that the methods and systems provided herein can be used to label nucleic acids with a number of agents including, but not limited to, backbone stains, and in particular mono-intercalating backbone stains, as will be discussed in greater detail herein.

In one aspect, the invention provides a method for uniformly labeling a nucleic acid with an intercalator comprising providing a capillary coupled to a microfluidic device, wherein the capillary comprises an intercalator, placing a first end of the capillary in a vessel comprising a nucleic acid, applying hydrodynamic or electrokinetic force sufficient to move the nucleic acid from the vessel through the capillary and to the microfluidic device, wherein flow of nucleic acid through the capillary is laminar.

In some embodiments, the nucleic acid is DNA.

In some important embodiments, the intercalator is a mono-intercalator. In some embodiments, the intercalator is a mono-cyanine intercalator. In some embodiments, the intercalator is positively charged at about neutral pH. In some embodiments, the intercalator is PO-PRO. In some embodiments, the intercalator is PO-PRO-1 or PO-PRO-3.

In some embodiments, the capillary comprises the intercalator in a buffered solution.

In some embodiments, the capillary has dimensions of about 15 cm in length and about 150 micron internal diameter. In some embodiments, the capillary is pre-filled with intercalator by hydrodynamic force. In some embodiments, the nucleic acid is labeled with the intercalator at a frequency of one intercalator molecule per three base pairs.

In some embodiments, the microfluidic device is coated with an electroosmotic flow (EOF) suppressor on one or more of its interior surfaces. In some embodiments, the capillary comprises an intercalator and an electroosmotic flow (EOF) suppressor in a buffered solution. In some embodiments, the electroosmotic flow (EOF) suppressor is a water soluble methylhydroxyethyl derivative of cellulose, polyvinylalcohol, polyvinylpyrrolidone, polyethyleneglycol or Triton X-100.

In some embodiments, an electrokinetic force is applied to move the nucleic acid and a cathode is present in a waste reservoir and an electrode is present in the vessel.

In some embodiments, the nucleic acid and intercalator move through the capillary in separate streams.

In another aspect, the invention provides a system comprising a microfluidic device coupled to one end of a capillary comprising an intercalator.

In some embodiments, the system further comprises a waste reservoir coupled to a vacuum. In some embodiments, the system further comprises a waste reservoir comprising a cathode.

In some embodiments, the intercalator is a mono-cyanine. In some embodiments, the intercalator is positively charged at about neutral pH. In some embodiments, the intercalator is PO-PRO. In some embodiments, the intercalator is PO-PRO-1 or PO-PRO-3. In some embodiments, the capillary comprises the intercalator in a buffered solution.

In some embodiments, the microfluidic device is coated with an electroosmotic flow (EOF) suppressor on one or more of its internal surfaces. In some embodiments, the capillary comprises an intercalator and an electroosmotic flow (EOF) suppressor in a buffered solution.

In some embodiments, the electroosmotic flow (EOF) suppressor is a water soluble methylhydroxyethyl derivative of cellulose, polyvinylalcohol, polyvinylpyrrolidone, polyethyleneglycol or Triton X-100.

In another aspect, the invention provides a method for uniformly labeling a nucleic acid with an intercalator comprising providing a microfluidic device comprising a sample inlet, a sheath fluid inlet, an elongation region, and a waste reservoir downstream of the elongation region, introducing a nucleic acid into the microfluidic device through the sample inlet, introducing intercalator into the microfluidic device through the sheath fluid inlet, and applying hydrodynamic force sufficient to move the nucleic acid from the sample inlet and the intercalator from the sheath fluid inlet through the elongation region to the waste reservoir, wherein flow of the nucleic acid and intercalator is laminar.

In some embodiments, the intercalator is a mono-cyanine. In some embodiments, the intercalator is positively charged at about neutral pH. In some embodiments, the intercalator is PO-PRO. In some embodiments, the intercalator is PO-PRO-1 or PO-PRO-3.

In some embodiments, intercalator is flowed through and is present in the microfluidic device prior to introduction of the nucleic acid. In some embodiments, the microfluidic device comprises two sheath fluid inlets positioned on opposite sides of the sample inlet, and intercalator is introduced into the microfluidic device through both sheath fluid inlets.

In some embodiments, the intercalator is present in a buffered solution. In some embodiments, nucleic acids are exposed to intercalator individually. In some embodiments, nucleic acids are exposed to the intercalator while under tension. In some embodiments, the nucleic acids are exposed to and bind with the intercalator while in the elongation region.

In some embodiments, nucleic acids are exposed to the intercalator for a time that is controlled by (1) fluid velocity through the microfluidic device and (2) geometry of the elongation region.

In some embodiments, the intercalator is present at a concentration ranging from about 50 nM to less than or about 10 μM, or from about 50 nM to about 500 nM, or from about 1 μM to less than or about 10 μM.

In some embodiments, the microfluidic device is coated on its interior surfaces.

In some embodiments, the nucleic acid and intercalator move through the elongation region in separate streams, optionally wherein there are 2-5 streams.

In another aspect, the invention provides a microfluidic device comprising a sample inlet port, a sheath inlet port, an elongation region, and a waste reservoir downstream of the elongation region, wherein the sheath inlet port and the elongation region comprise an intercalator prior to introduction of a nucleic acid sample. In some embodiments, the device comprises two sheath inlet ports positioned on opposite sides of the sample inlet port. In some important embodiments, the intercalator is a mono-cyanine. In some embodiments, the intercalator is positively charged at about neutral pH. In some embodiments, the intercalator is PO-PRO. In some embodiments, the intercalator is PO-PRO-1 or PO-PRO-3. The structure of PO-PRO-1 is provided in FIG. 12.

In another aspect, the invention provides a method for uniformly labeling a nucleic acid with an intercalator comprising providing a microfluidic chip comprising a sample inlet, an intercalator inlet, two sheath fluid inlets, an elongation region, and a waste reservoir downstream of the elongation region, wherein the intercalator inlet comprises two channels ("intercalator channels") extending therefrom and merging with a channel extending from the sample inlet ("sample channel") wherein the intercalator channels are positioned on opposite sides of the sample channel; and the two sheath fluid inlets are positioned on opposite sides of, and feed into, the elongation region, introducing a nucleic acid into the microfluidic chip through the sample inlet, introducing intercalator into the microfluidic chip through the intercalator inlet, and applying hydrodynamic force sufficient to move the nucleic acid from the sample inlet and the intercalator from the intercalator inlet through the elongation region to the waste reservoir, wherein flow of the nucleic acid and intercalator is laminar. In some important embodiments, the intercalator is a mono-cyanine. In some embodiments, the intercalator is positively charged at about neutral pH. In some embodiments, the intercalator is PO-PRO. In some embodiments, the intercalator is PO-PRO-1 or PO-PRO-3.

In another aspect, the invention provides a microfluidic device comprising a sample inlet, an intercalator inlet, two sheath fluid inlets, an elongation region, and a waste reservoir downstream of the elongation region, wherein the intercalator inlet comprises two channels ("intercalator channels") extending therefrom and merging with, and positioned on opposite sides of, a channel extending from the sample inlet ("sample channel"), and the two sheath fluid inlets are positioned on opposite sides of, and feed into, the elongation region.

The present invention further encompasses methods of making and/or using one or more of the embodiments described herein.

Other advantages and novel features of the present invention will become apparent from the following detailed description of various non-limiting embodiments of the invention when considered in conjunction with the accompanying Figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

Figure 1:
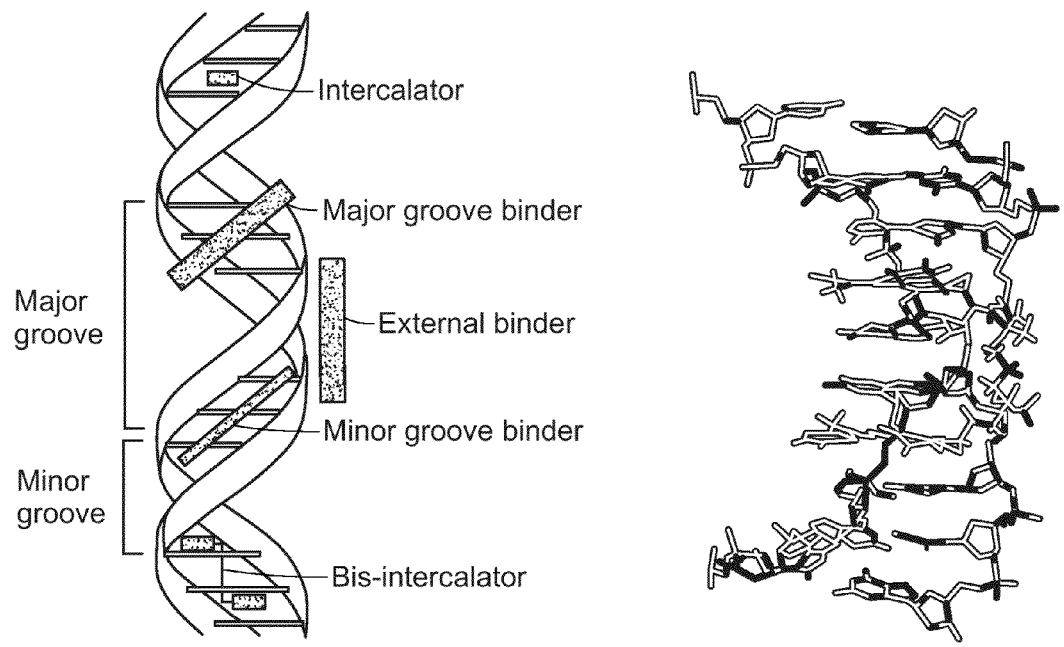
FIG. 1. The native conformation of DNA is shown here, as well as the varying positions where different types of intercalators may bind. A mono-intercalator is shown binding to the nucleic acid (see first red symbol shown at the top of the DNA helix). This is in contrast to the structure shown at the bottom which is a bis-intercalator.

Non-limiting embodiments of the present invention will be described by way of example with reference to the accompanying figures, which are schematic and are not intended to be drawn to scale. For purposes of clarity, not every component is labeled in every figure, nor is every component of each embodiment of the invention shown where illustration is not necessary to allow those of ordinary skill in the art to understand the invention.

DETAILED DESCRIPTION OF INVENTION

The invention provides methods and systems, including microfluidic devices, useful for uniformly labeling nucleic acids with an agent such as but not limited to a backbone stain even if the amount and concentration of nucleic acid being stained is unknown and/or is varied from sample to sample. As a result, the invention facilitates the labeling of nucleic acids since it avoids the need to quantitate nucleic acids prior to labeling.

The invention is described herein in the context of Direct Linear Analysis (DLA) or Genome Sequence Scanning (GSS™), for exemplary purposes. However it is to be understood that the methods and systems of the invention are not so limited and may be used in a variety of nucleic acid applications.

DLA or GSS™ involves analyzing a polymer such as a nucleic acid in a linear manner (i.e., starting from one end and moving along the length of the nucleic acid). The analysis detects signals along the length of the nucleic acid and determines their position along the length of the nucleic acid and their intensity. The signals are typically those from sequence non-specific backbone stains and sequence-specific agents such as oligonucleotides. Signals from sequence non-specific backbone stains are used to detect a nucleic acid and to visualize its length. Signals from sequence-specific agents are used to derive sequence information about the nucleic acid which in turn can be used to determine the identity of the nucleic acid and/or its relatedness to other nucleic acids and/or its source including its microbial source.

Importantly, DLA or GSS™ analyzes individual nucleic acids, yielding a profile for each analyzed nucleic acid. This is in contrast to methods that analyze a plurality of identical (or near-identical) nucleic acids. Accordingly, DLA or GSS™ can be performed on directly harvested nucleic acid samples without an intervening in vitro amplification (e.g., PCR step).

Uniform labeling of a nucleic acid across its backbone via a backbone specific (rather than a sequence specific) stain is important for DLA or GSS™ due to its use of the backbone staining to visualize the nucleic acid and to approximate its location (including the location of its "head" and "tail" ends) and its length. Thus, the invention, in certain aspects, provides methods and systems for uniform labeling of nucleic acids by sequence non-specific stains.

The invention therefore, in part, contemplates the labeling of individual nucleic acids as they move through a region populated by an intercalator. The nucleic acids are therefore labeled in this manner while they are in flow. This is in contrast to methods in which relatively immobile nucleic acids are labeled with an intercalator in a reaction vessel (such as a test tube or an Eppendorf tube) and then, after labeling, are placed in flow for analysis. The nucleic acids may or may not be pre-labeled with a sequence-specific agent (such as oligonucleotides). In some important embodiments, the nucleic acids are labeled with a sequence-specific agent while relatively immobile in a reaction vessel, and then are placed to flow through a solution that comprises an intercalator. The intercalator is provided in solution, such as a buffered solution. The solution, as its name implies, is a liquid rather than a solid or a semi-solid (such as a gel).

In some important instances, DLA or GSS™ is performed using mono-cyanine dyes as intercalators. Mono-cyanine dyes are characterized by lower affinity to DNA than their bis counterparts, discussed below, but otherwise share similar chemistries and spectral properties. Use of mono-cyanines, in some important instances, reduces the likelihood of intercalator-induced condensation, precipitation and aggregation, thereby eliminating or reducing the possibility of a single dye binding two molecules of DNA, and thus crosslinking them. Examples of mono-cyanines include but are not limited to the PO-PRO intercalators such as but not limited to PO—PRO-1 and PO-PRO-3. In some instances, the intercalator is positively charged at the pH at which the nucleic acid is analyzed. This pH is typically in the range of about 6-8. In some embodiments, the buffer is TE (tris-EDTA) buffer pH 8.

The region through which the nucleic acids flow may be in a microfluidic device or in a capillary coupled to a microfluidic device. The region is one which the nucleic acid flows through as it progresses towards an elongation region (where the nucleic acid is stretched) and ultimately an interrogation region (where the nucleic acid is exposed to a laser and where signals from the nucleic acid are detected), both of which are typically integral to the microfluidic device. Thus in some instances the region may be located partially or wholly within the elongation region. The fluid in the region moves through the region once a force such as a hydrodynamic or electrokinetic force is applied.

In some aspects, the nucleic acid and intercalator travel in essentially the same direction but in separate streams (or flows). The streams are arranged so that the nucleic acid stream is sheathed or surrounded by the intercalator stream, in some aspects. Labeling of the nucleic acid is thought to occur through the diffusion of the intercalator from its stream(s) to that of nucleic acid. Importantly, the streams are laminar in nature. Labeling in this manner has been found, in accordance with the invention, to ensure that the nucleic acids are uniformly and adequately labeled (and not overlabeled) regardless of the amount of nucleic acids in the sample. This is partly because the nucleic acids travel through regions comprising the intercalator individually. As a result it is possible to control the amount of nucleic acid that flows through the intercalator regions and ultimately to control the ratio of nucleic acid to intercalator without the need to determine the amount or concentration of nucleic acid in the sample. This means that the intercalator can be used at a concentration that is sufficient for adequate labeling of the nucleic acid but which is not introducing increased background signal or otherwise impeding the analysis.

Accordingly, the invention addresses issues that can arise when too little or too much intercalator is used in the labeling of a nucleic acid. When too little intercalator is used, the nucleic acid being analyzed may be under-labeled, potentially resulting in the nucleic acid not being detected in whole or in part. When too much intercalator is used, it can attach to the interior surfaces of the microfluidic device, thereby causing significant background signal. In addition, fused silica of which the microfluidic device may be comprised is also negatively charged, and positively charged intercalator at high concentrations can bind to it, causing enhanced fluorescence in the fluidics, as well as sticking of the nucleic acid to the intercalator-coated fused silica surface. DNA condensation can be reduced through the use of mono-cyanine dyes such as PO-PRO.

Figure 2:
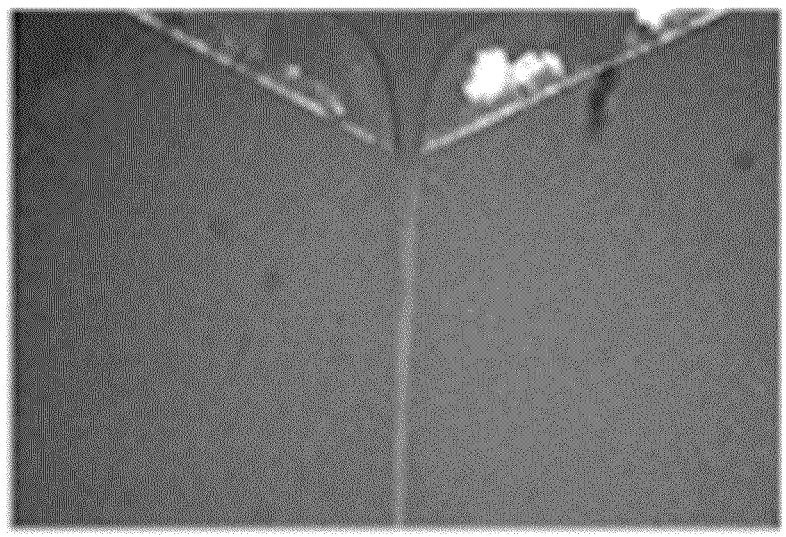
FIG. 2. On-chip intercalation using PO-PRO-1 eliminates DNA aggregation and surface sticking.

Thus, it was found in accordance with the invention that, in some instances, that cross-linking of DNA to other moieties such as other DNA or to surfaces such as glass surfaces within a microfluidic chip can be eliminated or reduced if the intercalation reaction was performed with a "mono-intercalator" such as but not limited to PO-PRO intercalators (e.g., PO-PRO-1 or PO-PRO-3). As used herein, a mono-intercalator intends a moiety that binds (typically non-covalently) with a DNA (or other nucleic acid) at a single site rather than at two sites, such as two adjacent sites. This is to be contrasted with a bi-intercalator (or bis-intercalator), such as a bis-cyanine intercalator, which binds to two separate but adjacent sites on a DNA. FIG. 1 illustrates such binding by a mono-intercalator and a bis-intercalator. FIG. 2 illustrates that on-chip intercalation using PO-PRO-1 eliminates DNA aggregation and surface sticking.

Mono-cyanine intercalators have reportedly lower affinity for DNA compared to their bis-counterparts. However, this reduced affinity did not impact the use of such mono-cyanine intercalators in the methods of the invention which involve sheathing of DNA with flow streams comprising excess intercalator. Thus, some embodiments of the invention utilize mono-cyanine intercalators in view of (a) their lower propensity to aggregate DNA and (b) the sheathing buffer scheme of the microfluidic devices contemplated by the invention.

The methods and devices of the invention are premised in part on the ability to perform on-chip intercalation without knowledge of and thus without dependence on the concentration of the intercalator used and the DNA being labeled. This is a significant advancement over the prior art methods that typically required that intercalator and DNA concentrations be known. In contrast, the methods of the invention can achieve intercalation even in the absence of such information. This means that samples may be processed without first measuring DNA content. This may be particularly useful for rare samples or samples with limited amount of DNA.

The ability to intercalate DNA from solutions of ranging DNA concentration is shown in the Examples. Briefly, solutions of varying DNA concentration were introduced into a microfluidic device having an elongation funnel, as described herein, and exposed to a fixed concentration of a mono intercalator in the sheathing buffer streams. In the Examples, 250 µM PO-PRO-1 was used. A uniform stretching coefficient for the 250.5 kB fragment was observed through a 32-fold dilution of stock DNA solution. This evidences that on-chip intercalation can be performed using a fixed intercalator concentration and a varying concentration of DNA, the latter of which may be known or unknown, without any appreciable effect on stretching. Accordingly, the data so generated can be used in linear DNA analysis methods, such as those described in published U.S. patent application US-2012-0283955-A1.

Figure 4A:
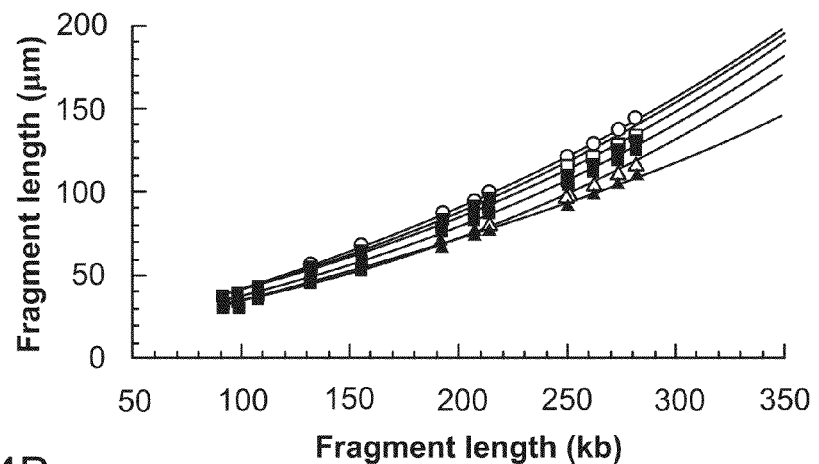
FIG. 4. Effect of intercalation of DNA stretching. (A) *E. coli* K12 NotI digested DNA was intercalated on-chip with increasing concentrations of PO-PRO-1 (▲ 50 nM, △ 100 nM, ■ 150 nM, □ 250 nM, ● 400 nM, ○ 500 nM). Observed molecule length (μm) is plotted as a function of known fragment length from sequence (in kb). (B) Stretching coefficient (μm/kb) for above conditions plotted as function of average molecule tension, as defined herein. (C) Stretching profile for DNA intercalated with PO-PRO-1 (triangles) compared to POPO-1 (squares) Duplicate data sets are presented and are indicated by open and closed symbols in (C).

The Examples further show experiments performed to determine optimal conditions for intercalation by varying the concentration of intercalator in the sheathing buffer. Briefly, DNA was run through a microfluidic device described herein with intercalator at concentrations ranging from 50-500 nM in the sheathing buffer streams. For each condition, fragment lengths (in µm) were determined for all restriction fragments by identifying each clustered fragment by its signature trace of site-specific probes. (Protozanova et al., Analytical Biochemistry, 2010. 402: p. 83-90.) When the measured fragment length (in µm) was plotted against the known fragment length in kb, characteristic quadratic stretching curves were observed (FIG. 4A). The extensibility of DNA increased with increasing PO-PRO-1 concentration.

The quadratic relationship between DNA extension and polymer length suggested that DNA extension was coupled to the tension on each molecule. The mechanism of DNA extension in GSS™ stretching funnels has been well characterized (Griffis et al., Lab Chip, 2013. 13(2): p. 240-51; Larson et al., Lab Chip, 2006. 6(9): p. 1187-99). The molecule velocity within the stretching funnel is the average of the fluid velocity along the length of the molecule. In the constant strain-rate funnel, the average fluid velocity occurs at the center of mass of the extended polymer, and fluid velocity increases linearly along the length of the molecule. The difference in velocity between the molecule and the fluid surrounding it at each segment along the length of the molecule results in a drag profile where the difference in velocities is greatest at the ends of the molecule and is zero at the center of the molecule. This results in a parabolic tension profile along the molecule, where the cumulative strain is maximal at the center of the molecule, and approaches zero at the ends. This is in contrast to the uniform tension profile generated in traditional strain loading techniques such as optical tweezers or AFM.

Figure 4B:
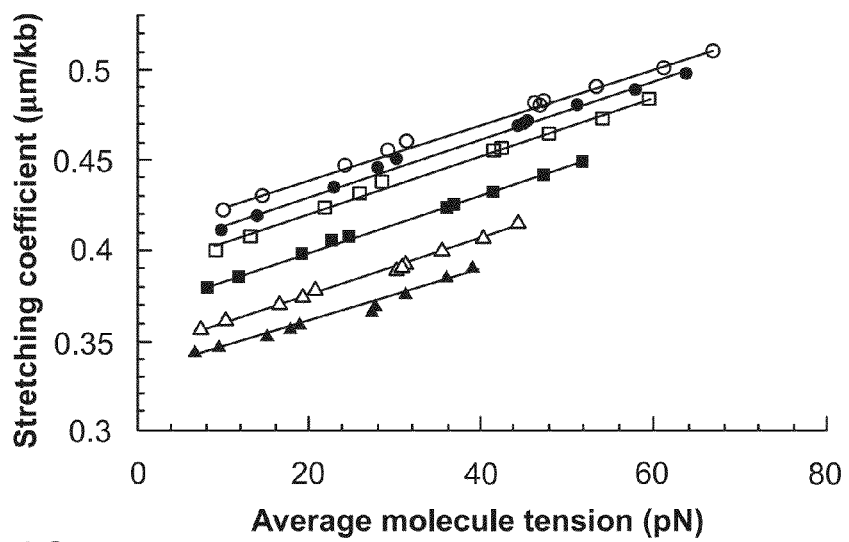
Figure 4C:
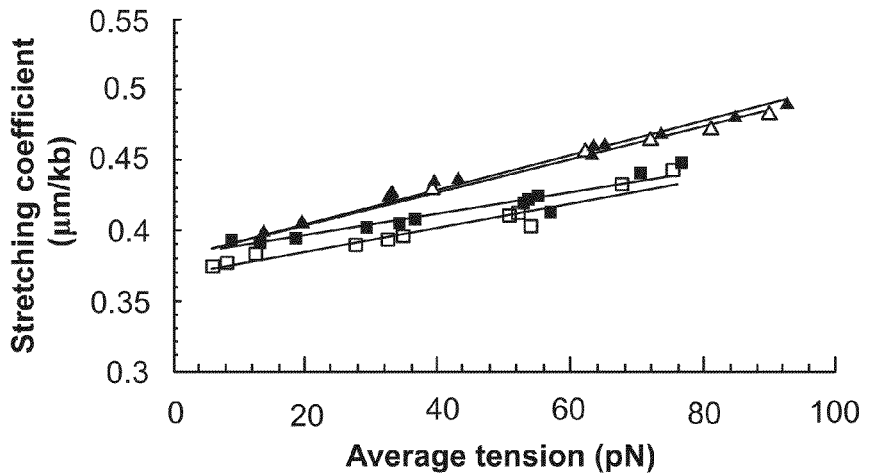

The peak tension $T_{max}$ along a molecule of length $L_{mol}$ is approximately:

$$T_{max} = \frac{1}{8}\zeta L_{mol}^2 \dot{\epsilon}(x)$$

where $\dot{\epsilon}$ is the strain rate in the stretching funnel, and $\zeta$ is the molecular drag coefficient (0.61 cP). The average tension is approximately ⅔ that value. The stretching coefficient for each fragment cluster, defined as the ratio of the measured length in µm to the known polymer length in kb, was plotted for experiments spanning a range of intercalator concentrations from 50 nM to 500 nM (FIG. 4B). These plots indicate that the DNA stretching coefficient is linearly dependent on the tension applied to each molecule. The slope of these plots does not vary with intercalator concentration, but the y axis intercept does increase with increasing intercalator concentration. These findings were based on stretching experiments performed with a mono intercalator (PO-PRO-1). DNA intercalated with the bis intercalator POPO-1, in contrast, had a significantly lower slope and that slope varied with intercalator concentration (FIG. 4C).

Accordingly, uniform DNA stretching can be achieved between experiments using on-chip intercalation, by fixing the concentration of intercalator added to the sheathing ports of the microfluidic device. From the data presented here, intercalation and DNA extension are determined by the intercalator concentration, but are unaffected by the concentration of DNA in a given sample. This differs from the DNA concentration dependency on stretching behavior observed using standard in-tube intercalation with POPO-1.

The Examples provides experiments that validate on-chip intercalation, particularly where a mono intercalator (e.g., PO-PRO-1) is introduced to a microfluidic chip sheathing buffer.

In the methods provided herein, individual DNAs are intercalated (one at a time) as each enters the DNA stretching funnel. These methods are preferably carried out, in some instances, using a mono intercalator such as PO-PRO-1, in order to eliminates or reduce DNA sticking to the glass chip. The methods therefore provide that DNA extension can occur independently of the DNA concentration using on-chip intercalation. The methods further provide that DNA extension is dependent on intercalator concentration, which can be fixed independently of knowing the DNA concentration.

The aspects and embodiments of the invention are exemplified in the context of intercalation of double stranded nucleic acids such as double stranded DNA. However, it is to be understood that the methods and devices described herein may be used for rapid, concentration-independent reaction of polymers with other ligands.

Various of the methods and systems of the invention will now be described in greater detail. These methods and systems allow for sufficient concentrations of labeling agents such as intercalators to be used in order to adequately label large masses of nucleic acids, thereby limiting or avoiding adverse effects that can occur when higher concentrations of labels are used (including for example over-intercalation) in the presence of lower masses of DNA. These methods and systems therefore facilitate analysis on a broad range of sufficiently intercalated DNA masses, among other things. Several implementations of microfluidic devices and their methods of use, in accordance with the invention, are described below.

In one aspect, the invention provides a capillary coupled to a microfluidic device that supports hydrodynamic or electrophoretic loading of nucleic acids in the presence of intercalator. In this aspect, the nucleic acid is exposed to the intercalator during the loading process (e.g., through the capillary that is used to load the nucleic acid onto the microfluidic device.

Figure 5:
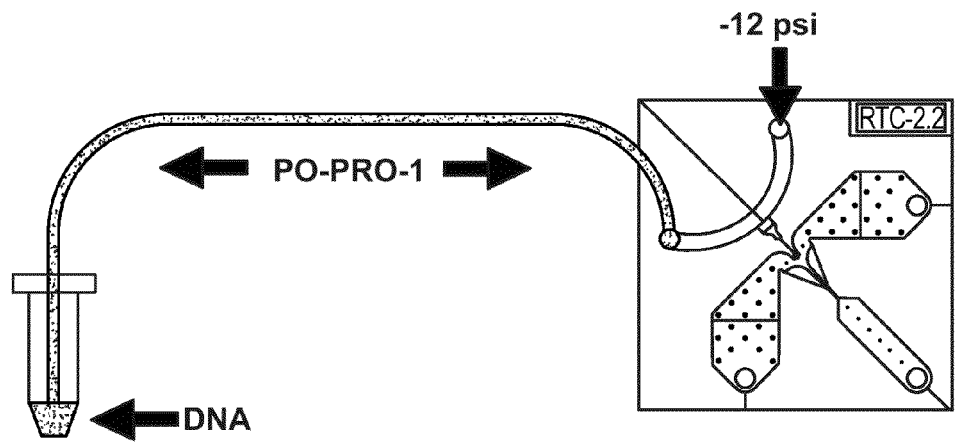
FIG. 5. A capillary is first connected to the 20 μm region of a RTC microfluidic device. The sample loop is filled with an intercalator such as PO-PRO-1, then introduced to the DNA sample. Vacuum is applied at the waste, and intercalation occurs via transverse lateral diffusion. The sample loop may be more deeply etched than other channels in the microfluidic chip. As an example, it may have a depth of about 20 microns as compared to other channels downstream from it which may have depths of about 2 microns. The microfluidic devices of the invention comprise microfluidic chips. The chip is illustrated by the square in the figures such as FIG. 5. The chips may vary in size. Exemplary chips are 8 mm×8 mm.

This aspect provides a system comprising a microfluidic device coupled to one end of a capillary comprising an intercalator. An example of such a system is shown in FIG. 5. As shown, one end of the capillary is coupled to the microfluidic device and the other end can be placed in a vessel that comprises the sample to be analyzed. The coupling of the capillary to the microfluidic device may be permanent or temporary. The capillary may be made of plastic (including PEEK, Ultem, or cyclic oleofins) or glass, although it is not so limited. The capillary length is not limiting. Capillary limiting diameter should be small to minimize diffusion distance. In some embodiments, the capillary may be about 15 cm long and have an internal diameter of about 150-500 microns.

Figure 6:
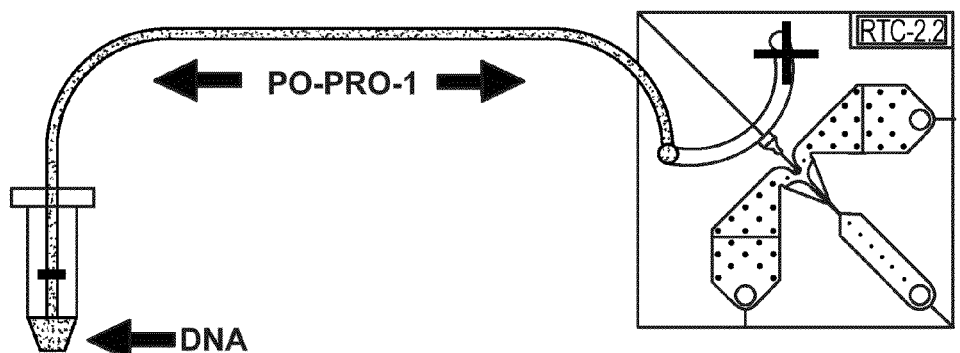
FIG. 6. Again, a capillary is connected to the 20 μm region of an RTC microfluidic device, and the sample loop is filled with an intercalator such as PO-PRO-1. Electrodes are then placed in the sample and waste ports, and current is driven across the system.

"A capillary comprising an intercalator" means the capillary houses a fluid that comprises an intercalator. The capillary comprises the intercalator prior to entry of the nucleic acid into capillary (i.e., the intercalator is present in the fluid held by the capillary). The capillary may be loaded with the fluid comprising the intercalator using hydrodynamic force (or pressure), for example by applying a vacuum downstream in the fluid path connected to the capillary. Thus, in some embodiments, the system comprises a vacuum downstream of the capillary. The vacuum may be coupled to a waste reservoir or to another inlet or outlet in the system including the microfluidic device that comprises a microfluidic chip. As used herein, the terms inlet and inlet port are used interchangeably, and the terms outlet and outlet port are used interchangeably. The capillary may be loaded with the fluid comprising the intercalator using electrokinetic force, for example by placing a cathode downstream of the capillary and placing an anode upstream of the capillary as shown in FIG. 6. The cathode may be in a waste reservoir and the anode may be in the vessel housing the sample prior to analysis also as shown in FIG. 6.

In various of the systems provided herein that incorporate electrokinetic force, the capillary and/or the microfluidic device comprises an electroosmotic flow (EOF) suppressor. EOF is the motion of liquid induced by an applied potential across a capillary tube, a microchannel, or any other fluid conduit. EOF is most significant in small channels, and can occur in buffered as well unbuffered (e.g., water) solutions. It is preferable to reduce or eliminate EOF during DLA and GSS™ and other microfluidic applications. An EOF suppressor is an agent that suppresses (partially or, more preferably, completely) EOF. Examples include but are not limited to water soluble methylhydroxyethyl derivative of cellulose, polyvinylalcohol, polyvinylpyrrolidone, polyethyleneglycol or Triton X-100. Other EOF suppressors are known in the art and the invention intends to embrace their use as well.

In some embodiments, the capillary and/or the microfluidic device is coated with an EOF suppressor on one or more of its interior surfaces (i.e., those surfaces that contact the solutions comprising the intercalator and/or nucleic acid. In some embodiments, the EOF suppressor is simply present in the solution comprising the intercalator and/or the nucleic acid. Thus, the solution housed by the capillary and/or the microfluidic device may comprise intercalator and buffer, and optionally also an EOF suppressor.

The intercalator is used at a concentration suitable for labeling the nucleic acid at a frequency of about one intercalator (molecule) per about three base pairs. In the electrokinetic loading scheme, the concentration of intercalator used could be in excess of the local concentration of DNA base pairs in order to saturate their appropriate binding sites. The opposite motilities of free intercalator and DNA in the presence of an electric field would serve to continuously separate the DNA from free intercalator.

The buffer may be any buffer having buffering capacity in the neutral pH range. An non-limiting example is tris buffer. Typically, the solution will also include divalent ion chelators such as EDTA in order to reduce the activity of nucleases such as DNase. Buffered solutions may include TE or Tris-Borate-EDTA (TBE). One of ordinary skill will be able to select an appropriate buffered solution for the particular application.

The invention therefore also provides, in another aspect, a method for uniformly labeling a nucleic acid with an intercalator comprising (1) providing a capillary coupled to a microfluidic device, wherein the capillary comprises an intercalator, (2) placing a first end of the capillary in a vessel comprising a nucleic acid, and (3) applying hydrodynamic or electrokinetic force sufficient to move the nucleic acid from the vessel through the capillary and into the microfluidic device. The flow of the nucleic acid through the capillary is laminar as is the flow of the intercalator.

In this as well as other aspects of the invention, the nucleic acid may be a double stranded nucleic acid such as but not limited to double stranded DNA. It will be understood that, when the methods and systems of the invention are used to label a nucleic acid with for example a sequence specific agent such as an oligonucleotide, the nucleic acid may be a single stranded nucleic acid such as single stranded DNA or RNA.

Depending on the embodiment, the capillary and chip are typically pre-filled with intercalator using hydrodynamic force. For example, a vacuum could be applied to ports 53 and 61 for capillary or chip loading respectively. The hydrodynamic or electrokinetic forces are also used to move the nucleic acid.

In the case of the hydrodynamic force, a vacuum (or negative pressure) may be applied downstream of the capillary (i.e., in a direction away from the sample vessel). In this embodiment, the nucleic acid is drawn through the intercalator, taking advantage of the parabolic flow profile in the narrow channel to sheath the nucleic acid with a thin layer of intercalator near the walls of the capillary, permitting rapid diffusion and staining of the nucleic acid.

In the case of the electrokinetic force, a cathode is present in a waste reservoir and an electrode is present in the vessel. In this embodiment, the nucleic acid and the intercalator will have opposite motilities in the presence of an electric field and therefore intercalator will be driven through the approaching front of the nucleic acid, staining the nucleic acid as it loads onto the chip.

Typically, the nucleic acid and intercalator move through the capillary and/or the microfluidic device in separate laminar streams, with the intercalator comprising solution sheathing the nucleic acid solution.

Two embodiments are illustrated in FIGS. 5 and 6. FIG. 5 illustrates a hydrodynamic loading approach while FIG. 6 illustrates an electrokinetic loading approach. In FIG. 5, the sample loop and the capillary are prefilled with intercalator in buffer. The sample loop is a relatively deep channel on the microfluidic chip (e.g., it may have a depth of about 20 microns). The available end of the capillary is then placed into the DNA sample of interest for hydrodynamic loading. The parabolic Poiseuille flow profile draws DNA through the intercalator present in the sample loop (including the capillary), sheathing it with a layer of fluorophore, and establishing conditions for transverse lateral diffusion. (Krylova et al., 2009)

This approach has several aspects of interest. First, replenishment of intercalator between runs is simplified, as the intercalator is loaded through the same path as the sample (i.e., intercalator loads through the same end as does the nucleic acid, thereby preventing contamination of the next sample by flushing the preceding sample back onto the chip with the next bolus of intercalator). It is also expected that the short time between intercalation and interrogation/detection limits the amount of nucleic acid condensation that can occur, in contrast for example to intercalation of nucleic acids in a reaction vessel prior to loading into the device itself. In view of this distinction, the intercalation of the invention may be thought of as being "real-time" intercalation since intercalation occurs during the process of introducing the nucleic acid into the microfluidic device, into the elongation region of the device and/or through this region, as will be described in more detail below. In addition, the small cross-sectional volumes of the capillary (e.g., about 150 micron internal diameter) and the 20 μm cross channel sample loop may locally isolate individual nucleic acids, constraining them and thereby limiting condensation. In addition, low level adhesion of intercalator at the interior surfaces of the capillary or microfluidic chip surface may serve as a reservoir for intercalator replenishment with each loading cycle.

FIG. 6 illustrates the same microfluidic chip and capillary setup as in FIG. 5 except that the hydrodynamic loading is replaced with electrokinetic loading and intercalation. (Krylova et al. 2009) In the approach illustrated in FIG. 6, TE buffer containing intercalator is loaded hydrodynamically into the sample loop. The nucleic acid sample is then introduced to the capillary, with an anode in the sample vessel and a cathode at the cross flush waste reservoir. When current is applied, electrophoresis occurs. Negatively charged nucleic acid travels onto the chip, toward the waste, while positively charged intercalator migrates toward the sample vessel. The resulting cross flow assures a continuous stream of intercalator over the nucleic acid, as well as potential displacement of poorly bound intercalator. Because of the intrinsically charged surfaces in the microfluidic devices (e.g., those made from fused silica, among others), electroosmotic flow (EOF) may compromise electrokinetic nucleic acid loading. To address this possibility, the device may be pre-coated with an EOF suppressor or an EOF suppressor may be included in the intercalator containing solution.

In another implementation of in-capillary intercalation, intercalator is included in a leading buffer, and the sample in a sample buffer is loaded onto the chip by isotachophoresis (ITP). (Jung, Bharadwaj et al. 2006; Shackman and Ross 2007) The loading condition for this approach is established similarly to the electrokinetic scheme described above. Differential anionic mobilities between the leading and sample buffers focus nucleic acids at the moving interface between the buffer types, resulting in the concentration of nucleic acids at the interface between the buffers. Additionally, the inclusion of intercalator as a cationic component of the leading buffer allows for simultaneous intercalation. It has been found that if the intercalator is positively charged then although the nucleic acids concentrate at the interface between the buffers, the intercalator travels across the region of concentrated nucleic acids. In these embodiments, nucleic acid intercalation can be combined with concentration of the nucleic acids.

Figure 7:
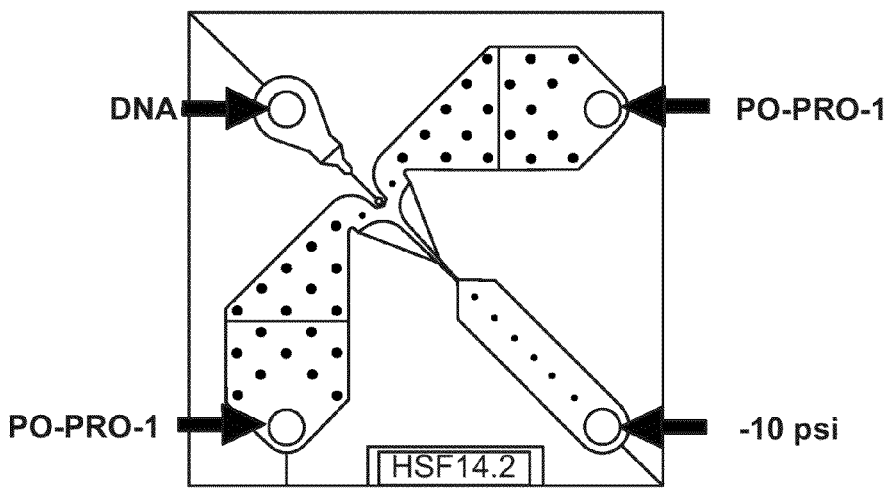
FIG. 7. DNA is loaded into the sample injection port, and TE containing an intercalator such as PO-PRO-1 is loaded into the sheathing buffer ports. The system is then driven under vacuum. DNA is introduced to the intercalator as it enters the interrogation region, and intercalation occurs.
Figure 9:
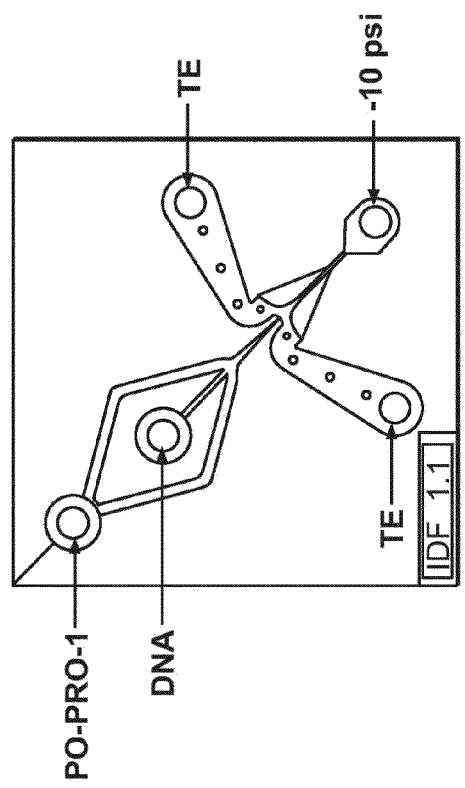
FIG. 9. An intercalator such as PO-PRO-1, DNA, and sheathing buffer such as TE are introduced to their respective loading ports. When vacuum is applied at the waste, laminar flow brings the intercalator and DNA into contact, and the short diffusion distance allows them to mix within milliseconds. Full seconds pass between mixing and the introduction of DNA to the detection region. The residence time of nucleic acids in this configuration is about 3-8 seconds. This could be increased by increasing the flow rate through the sheath inlets as doing so reduces the flow of nucleic acid and keeps the nucleic acids together with the intercalator for a longer period of time.
Figure 11:
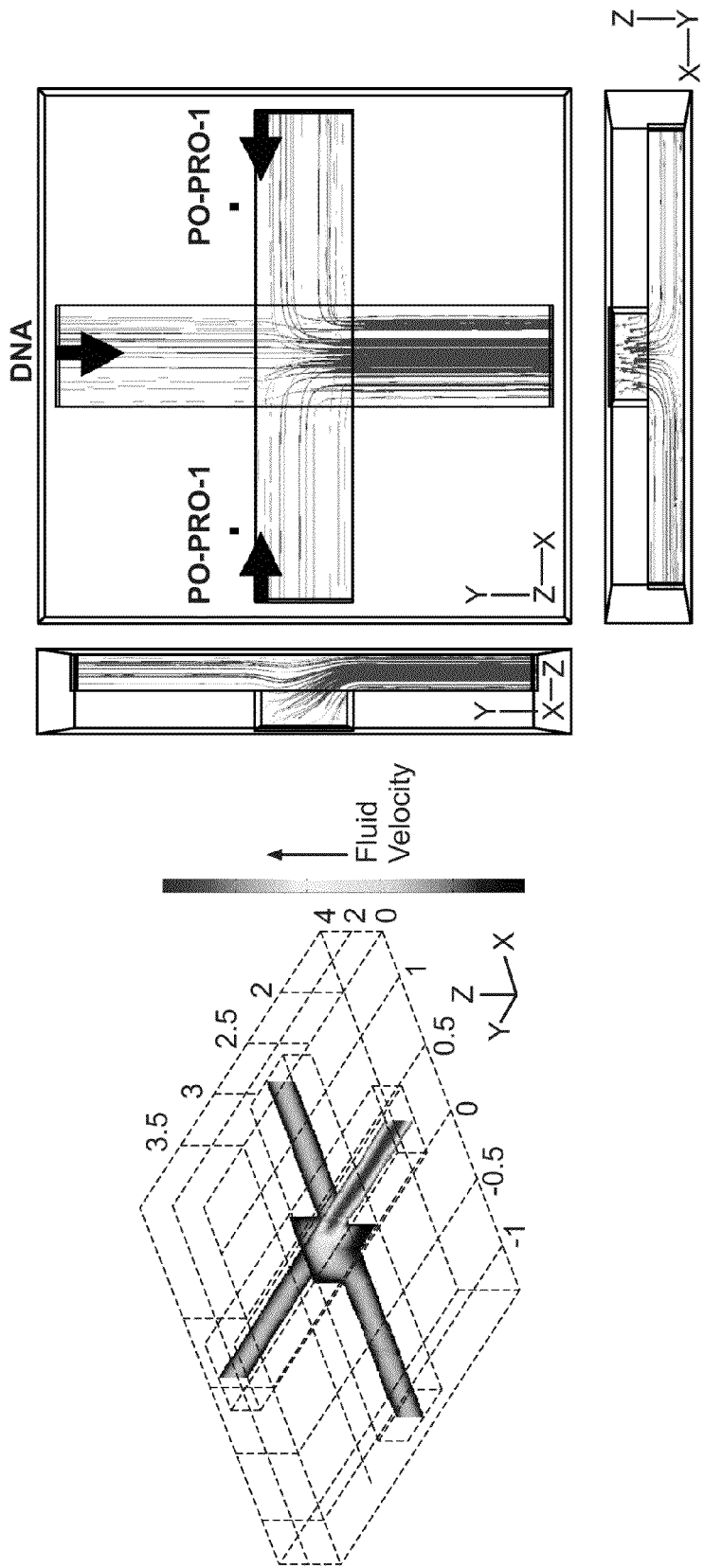
FIG. 11. 3D COMSOL fluid velocity simulation of the proposed multi-planar geometry, and projection views of the three dimensional streamlines. Laminar flow of intercalator (such as PO-PRO-1) from the bottom 2 μm cross channel interfaces with the upper DNA injection channel, and passes through the outlet. The total diffusion distance where the two intersect is 1 μm.
Figure 12:
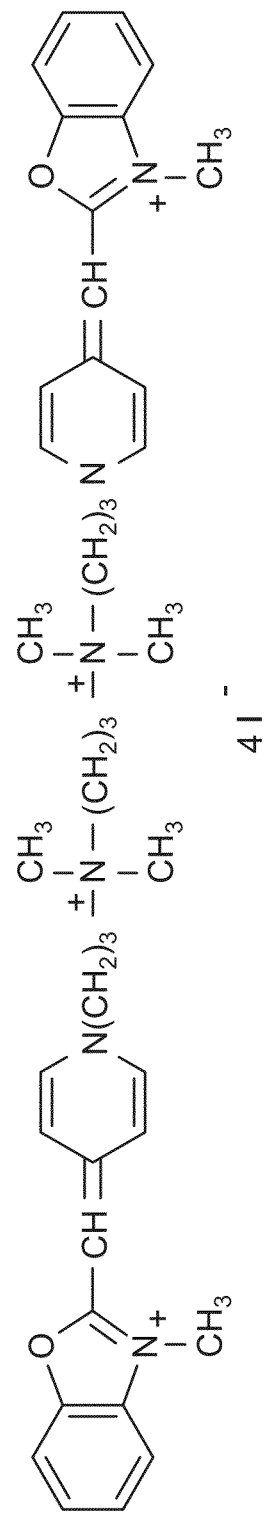
FIG. 12 provides the chemical structures of POPO-1 and PO-PRO-1.
Figure 12:
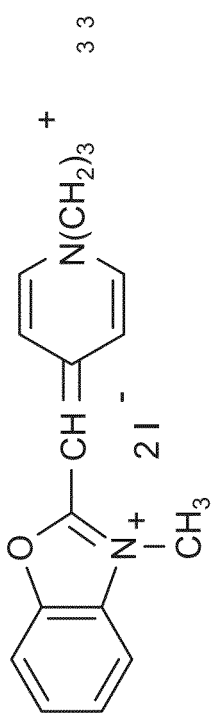

The invention also contemplates performing the intercalation reaction within the confines of shallow-etched microfluidic channels. This is referred to herein as "on-chip intercalation". In some embodiments, the intercalation reaction may be confined to a 2 micron deep channel. It could however be performed in deeper channels (e.g., on the order of 100 micron microchannels). This approach can provide, in some instances, more precise control over kinetics of the intercalation reaction. Due to laminar flow, short diffusion distances, and small mass diffusion coefficients, the extent of completion of the intercalation reaction can be closely monitored and adjusted. Embodiments of this approach are illustrated in FIGS. 7, 9 and 11. These approaches have been shown to provide rapid, uniform intercalation on a microfluidic device.

One embodiment provides a microfluidic device comprising a microfluidic chip that itself comprises a sample inlet port, a sheath inlet port, an elongation region, and a waste reservoir downstream of the elongation region, wherein the sheath inlet port and the elongation region comprise an intercalator prior to introduction of a nucleic acid sample. As illustrated in FIG. 7, the chip may comprise two sheath inlet ports and preferably they are positioned on opposite sides of the sample inlet port. As used herein, when two sheath inlet ports are positioned on opposite sides of a sample inlet port, this means that one of the two sheath inlet ports is on one side of the sample inlet port and the other sheath inlet port is on the other side of the sample inlet port. This is illustrated in FIG. 7. The positioning of the sheath inlet ports preferably is equidistant from the sample inlet port, as the sheath fluid from such ports is used to position the nucleic acids centrally within the elongation and interrogation and detection regions of the chip. The sample inlet port, as its name implies, is the port through which the sample, including the nucleic acid, enters the chip. Similarly, the sheath inlet port is the port through which the sheath fluid enters the chip. The elongation region is the region on the chip through which the nucleic acid travels and in the process becomes elongated (or stretched). Elongation regions are known in the art and reference may be made to published application US-2004-0166025-A1 and Griffis et al., Lab Chip, 2013. 13(2): p. 240-51 for examples of elongation regions. In some embodiments, the elongation region is a funnel that narrows in the direction of the interrogation/detection region.

FIG. 13 provides one illustrative embodiment in which the device 10 includes an elongation structure that is formed into a chip. As shown, the device 10 may include four ports and may include a sample loading port 30, two sheath buffer channels 40, 50, the elongation structure 60 (may also be called the DNA stretching funnel), and a waste port 70. As illustrated, in one embodiment, there is a delivery channel 32 between the sample loading port 30 and the elongation structure, and there are two opposing buffer channels 40, 50 that also lead into the elongation structure.

The DNA stretching funnel 60 geometry was optimized based upon experimental results. In one illustrative embodiment, the structure of the funnel 60 is divided into two distinct regions or zones. The first zone 62 may be defined as the stretching portion of the funnel, and the second zone 64 may be defined as the detection region. The first zone 62 may have a first tapered shape, and the second zone 64 may have a second tapered shape, different from the first zone. Distinct taper definitions may be required for each region. The overall funnel geometry may therefore be fully described by three characteristic widths ($w_1$=width of first end of tapered channel, $w_2$=width of tapered channel at transition between first zone 62 and second zone 64, and $w_3$=width of tapered channel at the second end of the tapered channel), two characteristic lengths ($l_1$=length of first zone, and $l_2$=length of second zone), and two taper definition equations. These geometries are detailed in FIG. 13B.

Previous studies have demonstrated that DNA stretching is most uniform when the initial DNA extension occurs gradually in an increasing-strain rate funnel. In some embodiments, the geometry of the first zone 62 (the stretching portion) of the funnel may be described by the following equations:

$$w(x) = \frac{1}{(bx+c)^2} \quad \text{Equation 1}$$

$$b = \frac{1}{l_1}\left(\sqrt{1/w_2} - \sqrt{1/w_1}\right)$$

$$c = \sqrt{1/w_1}$$

Where the width of the channel (w(x)) is a function of the distance along the funnel ($l_1$), the initial funnel width ($w_1$) and the width at the transition between the stretching and detection portions of the funnel ($w_2$).

In some embodiments, the geometry of the first zone 62 of the funnel may be described by the following equations:

$$w(x) = \frac{2w_i v_i}{\alpha x^2} = \frac{F_1}{x^2} \quad \text{Equation 2}$$

$$F_1 = \frac{2v_x w_x x}{\dot{\varepsilon}_x}$$

Where the width of the channel w(x) is a function of the distance along the detection channel (x), the width at arbitrary position i ($w_i$), and the fluid velocity at arbitrary position i ($v_i$). $F_1$, which describes the geometrical taper coefficient for an increasing strain rate funnel, is a function of the distance along the detection channel (x) the fluid velocity at distance x ($v_x$), the funnel width at distance x ($w_x$), and the strain rate at distance x ($\dot{\varepsilon}$). The funnel taper geometry can be solved to provide a desired strain rate at any given fluid velocity.

Figure 13A:
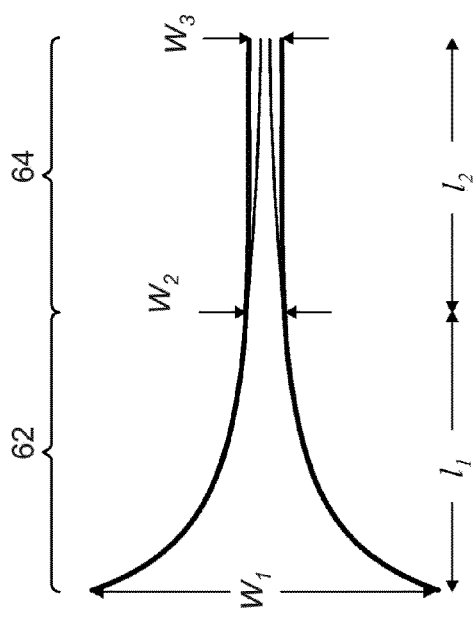
FIGS. 13A-13D provide a schematic representation of a microfluidic chip with an elongation structure according to one embodiment (FIG. 13A); a schematic representation of a tapered channel with two zones according to one embodiment (FIG. 13B); a schematic representation of a DNA sample being stretched in a tapered channel according to one embodiment (FIG. 13C); and a representative fluorescent signal plot generated from a single stretched DNA molecule (FIG. 13D).
Figure 13B:
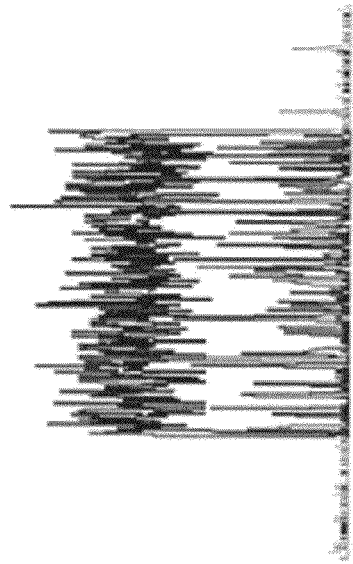

Previously described DNA stretching funnels utilized a parallel walled detection channel, which imposed a constant-velocity fluid profile in this region. For such funnels, $w_3=w_2$. This type of second zone 64 configuration is illustrated in FIG. 13B. In one experimental study, a novel detection channel geometry was also investigated, in which the increasing strain rate funnel transitions smoothly into a tapered detection channel with a constant-strain rate taper. This unique second zone 64 tapered configuration is also illustrated in FIG. 13B. In some embodiments, the geometry of the second zone 64 (the detection region) of the funnel may be described by the following equations:

$$w(x) = \frac{w_2}{1+x/a} \quad \text{Equation 3}$$

$$a = \frac{l_2}{w_2/w_3 - 1}$$

Where the width of the channel w(x) is a function of the distance along the detection channel (x), the width at the interface with the stretching portion of the funnel ($w_2$), and the final funnel width ($W_3$).

In some embodiments, the geometry of the second zone 64 of the funnel may be described by the following equations:

$$w(x) = \frac{F_2}{x} \quad \text{Equation 4}$$

$$F_2 = \frac{v_x w_x}{\dot{\varepsilon}}$$

Where the width of the channel w(x) is a function of the distance along the detection channel (x) and the constant strain rate taper coefficient $F_2$. $F_2$ is a function of the fluid velocity at distance x ($v_x$), the funnel width at distance x ($w_x$), and the strain rate ($\dot{\varepsilon}_x$).

Figure 13C:
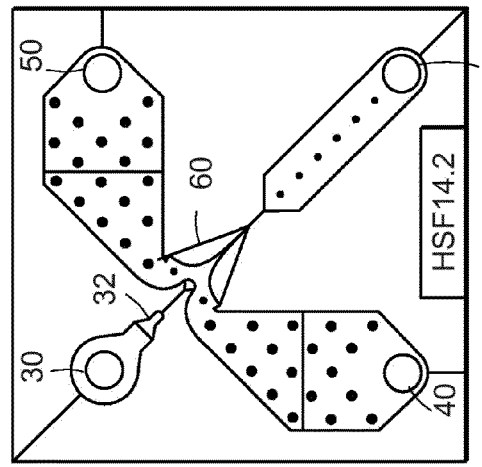
Figure 13D:
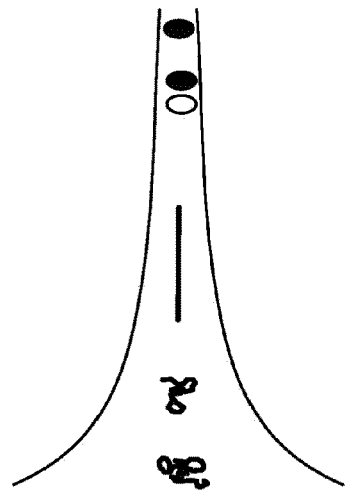

FIG. 13C illustrates a DNA sample passing through the elongation structure 60 and being stretched in the tapered channel.

In the interrogation/detection region, the nucleic acid is exposed to light of one or more wavelengths, typically as provided by a laser. In some embodiments, the interrogation region comprises three lasers, two of which are tuned to excite two different fluorophores on different sequence-specific agents bound to the nucleic acid, and one of which is tuned to excite the intercalator. As an example, the PO-PRO-1 intercalator is excited using a 488 nm argon laser, and the remaining two lasers excite fluorophores in the green and red spectrums. Signals from the nucleic acid are detected by one or more detectors in the interrogation/detection region. The detectors include a detector for the intercalator signals and optionally a detector for signals from the sequence-specific agents bound to the nucleic acid (e.g., fluorescently labeled oligonucleotides). In an important embodiment, the intercalator is a mono-cyanine dye such as PO-PRO-1.

These embodiments envision the placement and presence of intercalator containing solution in the microfluidic chip prior to the introduction of the nucleic acids. The intercalator solution may be continually applied to the microfluidic chip through the sheath inlet port(s). As noted in FIG. 7, a vacuum (or negative pressure) may be applied downstream of the elongation and interrogation/detection regions. The hydrodynamic force moves the nucleic acid, intercalator and solution through the chip towards a waste reservoir downstream of the detection region. In some instances, the nucleic acid contacts the intercalator at the elongation region. In some instances, the nucleic acid contacts the intercalator as it enters the interrogation region, after it has been elongated. Depending on the nature of the elongation region and the particular chip, it is also possible that the elongation region is integral to the interrogation region.

This chip configuration may be used in a method for uniformly labeling a nucleic acid with an intercalator that comprises (1) providing a microfluidic device comprising a microfluidic chip comprising a sample inlet, a sheath fluid inlet, an elongation region, and a waste reservoir downstream of the elongation region, (2) introducing intercalator into the microfluidic device through the sheath fluid inlet, (3) introducing a nucleic acid into the microfluidic chip through the sample inlet, and (4) applying hydrodynamic force sufficient to move the nucleic acid from the sample inlet and the intercalator from the sheath fluid inlet through the elongation region to the waste reservoir, wherein flow of the nucleic acid and intercalator is laminar. It will be understood that in some embodiments, the intercalator is flowed through and is present in the microfluidic to device prior to introduction of the nucleic acid. As discussed herein, the microfluidic chip may comprise two sheath fluid inlets positioned on opposite sides of the sample inlet, and intercalator may be introduced into the microfluidic chip through both sheath fluid inlets.

This approach allows nucleic acids to be exposed to intercalator individually, meaning that the nucleic acids are not in physical contact with each other and even more preferably are sufficiently separated from each other so that each nucleic acid has relatively equivalent exposure to intercalator. The nucleic acids may be exposed to the intercalator while under tension (i.e., while they are entering and/or within the elongation region. The method may also comprise modulating the time the nucleic acid is exposed to the intercalator by modulating fluid velocity through the chip and/or the geometry of the elongation region. In some instances, the intercalator is present at a concentration ranging from about 50 nM to about 500 nM, about 100 nM to less than about 10 µM, or from about 50 nM to about 10 µM. The nucleic acid and intercalator may move through the elongation region in separate streams.

FIG. 7 illustrates an embodiment of sheath flow intercalation. In this embodiment, a high concentration of intercalator (relative to the concentration of DNA base pairs present in the given fluid volume) in tris-EDTA (TE) is introduced onto the chip through the sheath inlet ports. Intercalation at concentration ranging from 100 nM to less than 10 microns are suitable. In one embodiment, the intercalator PO-PRO-1 is used at a concentration near 300 nM. As nucleic acid is injected into the elongation region, it is sheathed with intercalator-containing buffered solution. Diffusion of the intercalator into the central stream (which comprises the sample and thus the nucleic acid) then initiates staining of the nucleic acid.

There are several advantages to this mode of intercalation. First, nucleic acids are exposed to the intercalator individually (i.e., one at a time), minimizing intermolecular aggregation. Second, the nucleic acid is maintained under tension during the reaction process, minimizing intramolecular aggregation via charge-negation. Third, the reaction time between nucleic acid and intercalator is a function of the fluid velocity and elongation region (e.g., funnel) geometry, and thus it can be tightly controlled.

Figure 8:
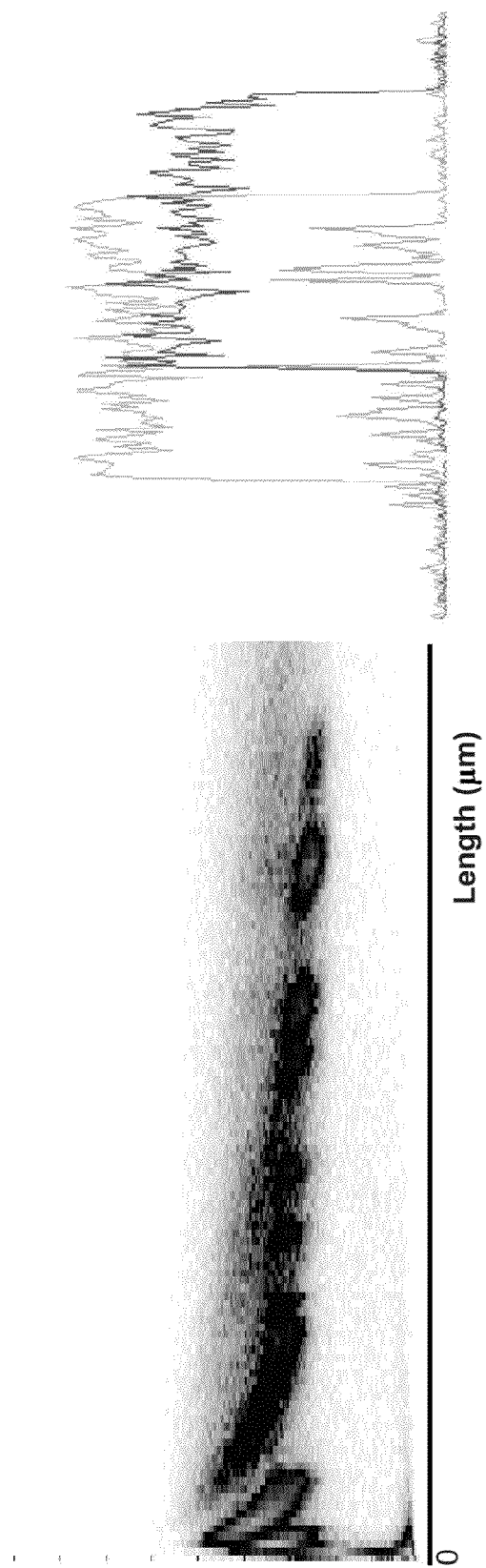
FIG. 8. DNA is partially stained over the 300 ms it spends in the presence of an intercalator such as POPO-1. However, the ends are never fully elongated and require a longer reaction time to be fully intercalated. This can be seen in the curved intensity profile of the DNA backbone. The plot is an average intensity per unit length versus length plot.

This mode of intercalation has been tested and its feasibility has been demonstrated as illustrated in FIG. 8. While some degree of incomplete staining of individual nucleic acids was observed, this was thought due to the short reaction times. This can be addressed and intercalation could be enhanced by decreasing the velocity of the sheath and sample moving through the chip and/or by increasing intercalator concentration with the proviso that at intercalator concentrations greater than 10 µM (e.g., for PO-PRO-1) rapid coating of the microfluidic device can occur, leading to increased background fluorescence. As discussed herein, an EOF suppressor may be used to reduce non-specific binding of the intercalator and the consequent background fluorescence.

Alternatively, another chip geometry may be used to facilitate intercalation. An example of one such geometry is illustrated in FIG. 9. That geometry is generally described as a microfluidic device comprising a microfluidic chip comprising a sample inlet, an intercalator inlet, two sheath fluid inlets an elongation region, and a waste reservoir downstream of the elongation region, wherein the intercalator inlet comprises two channels ("intercalator channels") extending therefrom and merging with, and positioned on opposite sides of, a channel extending from the sample inlet ("sample channel") and the first and second sheath fluid inlets are positioned on opposite sides of, and feed into, the elongation region.

Using this geometry, a method may be used for uniformly labeling a nucleic acid with an intercalator that comprises (1) providing a microfluidic device comprising a sample inlet, an intercalator inlet, two sheath fluid inlets, an elongation region, and a waste reservoir downstream of the elongation region, wherein the intercalator inlet comprises two intercalator channels extending therefrom and merging with the sample channel wherein the intercalator channels are positioned on opposite sides of the sample channel; and the sheath fluid inlets are positioned on opposite sides of, and feed into, the elongation region, (2) introducing a nucleic acid into the microfluidic device through the sample inlet, (3) introducing intercalator into the microfluidic device through the intercalator inlet, and (4) applying hydrodynamic force sufficient to move the nucleic acid from the sample inlet and the intercalator from the intercalator inlet through the elongation region to the waste reservoir, wherein flow of the nucleic acid and intercalator is laminar.

Figure 10:
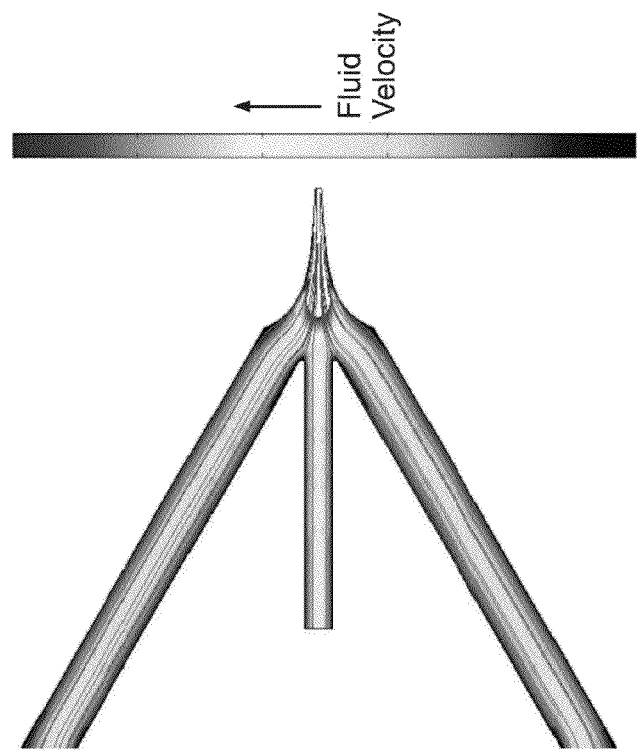
FIG. 10. 2D COMSOL fluid velocity simulation of the mixing geometry interface, where DNA is nested between adjacent intercalator (such as PO-PRO-1) streams.

FIG. 9 provides an example of this on-chip intercalation approach. In this example, separate ports are loaded with nucleic acid, intercalator and sheath fluid (or running buffer, as the terms are used interchangeably). The nucleic acid (or sample) stream is nested between two adjacent intercalator streams within the microfluidics as shown in FIG. 10. Subsequently, the three flows pass through the elongation region (e.g., a stretching funnel). This scheme takes advantage of the fluidic extension of nucleic acid in the presence of intercalator (as does the approach of FIG. 7), it uses the 2 µm etch depth in the chip channel to limit condensation, and it also incorporates an additional incubation channel to increase the time in which the nucleic acid is exposed to the intercalator. Additionally, downstream flow focusing can also be used to prolong the intercalation reaction until completion, in order to reduce intercalator concentrations to suitable levels.

In yet another embodiment, separate ports are again loaded with nucleic acid, intercalator and sheath fluid. This embodiment is illustrated in FIG. 11. The fluidics of this embodiment route the intercalator and nucleic acid streams into two separate perpendicular channels, vertically offset from each other. At their intersection, laminar flow preserves the parallel planar relationship between the two, and the total diffusion distance between the intercalator stream and the nucleic acid stream is reduced to half the channel height (i.e., the geometry consists of two crossing channels of height H and at the intersection of the two channels the total height is 2H). Due to small mass diffusion coefficients, this allows for near instantaneous onset of the intercalation reaction, and provides uniform access between the nucleic acid and the intercalator, regardless of the position of any given nucleic acid in the sample fluidic layer.

The microfluidic devices and configurations provided by the invention are intended to promote in-capillary or on-chip intercalation in order to enhance non-specific labeling of nucleic acids, regardless of the concentration of nucleic acid present in a given sample. All of these devices operate under laminar flow conditions. Device geometries have been optimized to maximize diffusion rates by performing the intercalation reactions in small volume microfluidic channels. As discussed herein, these devices and methods may also be used to promote and/or enhance binding between nucleic acids and other binding partners such as oligonucleotides, ligands, enzymes, and the like.

The invention may be practiced using a variety of intercalators.

Examples of mono intercalators include PO-PRO-1, BO-PRO-1, YO-PRO-1, TO-PRO-1, JO-PRO-1, PO-PRO-3, BO-PRO-3, YO-PRO-3, TO-PRO-3, TO-PRO-S.

The invention further contemplates use of other DNA-ligand interactions as well.

Examples of other intercalators that may be used in some instances include cyanine dyes such as SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red).

Examples of other intercalators that may be used in the methods and systems described herein include phenanthridines and acridines (e.g., ethidium bromide, propidium iodide, hexidium iodide, dihydroethidium, ethidium homodimer-1 and -2, ethidium monoazide, and ACMA); minor grove binders such as indoles and imidazoles (e.g., Hoechst 33258, Hoechst 33342, Hoechst 34580 and DAPI); and miscellaneous nucleic acid stains such as acridine orange (also capable of intercalating), 7-AAD, actinomycin D, LDS751, and hydroxystilbamidine.

In various embodiments of the invention, it may be preferable to use intercalators and/or other backbone stains that are not capable of crosslinking DNA and other nucleic acids, either covalently or non-covalently. The use of such intercalators or backbone stains reduces or eliminates DNA non-specific adhesion to glass surfaces such as those in a microfluidic chip or device.

The methods provided herein may involve the use of agents that bind to a nucleic acid in a sequence-specific manner "Sequence-specific" when used in the context of a nucleic acid means that the agent recognizes a particular linear (or in some instances quasi-linear) arrangement of nucleotides. "Specific binding" means the agent binds with greater affinity to a particular nucleic acid or a region within a particular nucleic acid than it does to other nucleic acid or other nucleic acid regions. It should be possible to achieve conditions under which the agent binds predominantly (or only) to its cognate nucleic acid sequence. Such "stringent hybridization conditions" are known in the art. (See for example Maniatis' Handbook of Molecular Biology.)

Any agent that is capable of recognizing a nucleic acid with sequence specificity (whether through complementary nucleic acid hybridization or through structural recognition based on particular nucleotide sequence can be used as a sequence-specific agent. In some instances, the agent is nucleic acid in nature and binds to a target nucleic acid via Watson-Crick binding. In other instances, the nucleic acid agent can bind to a target nucleic acid via Hoogsteen binding, thereby typically forming a triplex. In some instances, the nucleic acid probes can form both Watson-Crick and Hoogsteen bonds with the nucleic acid target. BisPNA probes, for instance, are capable of both Watson-Crick and Hoogsteen binding to a nucleic acid.

The sequence specific agents may be nucleic acids, including oligonucleotides, nucleic acid aptamers, PNAs such as bisPNAs, pcPNAs, ssPNAs, LNAs, DNAs, RNAs, co-nucleic acids such as DNA-LNA co-nucleic acids, siRNA, shRNA, proteins or peptides including antibodies and antigen-binding antibody fragments, etc.

The sequence-specific agents may be inherently or intrinsically labeled with a detectable label. Typically, for the sake of convenience, the detectable label is selected so that it can be detected using the same detector type used to detect the intercalator signals. Thus, typically, the detectable labels are fluorophores. More specifically, the detectable label may be selected from the group consisting of directly detectable labels such as a fluorescent molecule (e.g., fluorescein, rhodamine, tetramethylrhodamine, R-phycoerythrin, Cy-3, Cy-5, Cy-7, Texas Red, Phar-Red, allophycocyanin (APC), fluorescein amine, eosin, dansyl, umbelliferone, 5-carboxyfluorescein (FAM), 2'7'-dimethoxy-4'5'-dichloro-6-carboxyfluorescein (JOE), 6 carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), 5-(2'-aminoethyl) aminonaphthalene-1-sulfonic acid (EDANS), 4-acetamido-4'-isothiocyanatostilbene-2,2' disulfonic acid, acridine, acridine isothiocyanate, r-amino-N-(3-vinylsulfonyl)phenylnaphthalimide-3,5, disulfonate (Lucifer Yellow VS), N-(4-anilino-1-naphthyl)maleimide, anthranilamide, Brilliant Yellow, coumarin, 7-amino-4-methylcoumarin, 7-amino-4-trifluoromethylcouluarin (Coumarin 151), cyanosine, 4',6-diaminidino-2-phenylindole (DAPI), 5',5"-diaminidino-2-phenylindole (DAPI), 5',5"-dibromopyrogallol-sulfonephthalein (Bromopyrogallol Red), 7-diethylamino-3-(4'-isothiocyanatophenyl)-4-methylcoumarin diethylenetriamine pentaacetate, 4,4'-diisothiocyanatodihydro-stilbene-2,2'-disulfonic acid, 4,4'-diisothiocyanatostilbene-2,2'-disulfonic acid, 4-dimethylaminophenylazophenyl-4'-isothiocyanate (DABITC), eosin isothiocyanate, erythrosin B, erythrosin isothiocyanate, ethidium, 5-(4,6-dichlorotriazin-2-yl) aminofluorescein (DTAF), QFITC (XRITC), fluorescamine, IR144, IR1446, Malachite Green isothiocyanate, 4-methylumbelliferone, ortho cresolphthalein, nitrotyrosine, pararosaniline, Phenol Red, B-phycoerythrin, o-phthaldialdehyde, pyrene, pyrene butyrate, succinimidyl 1-pyrene butyrate, Reactive Red 4 (Cibacron® Brilliant Red 3B-A), lissamine rhodamine B sulfonyl chloride, rhodamine B, rhodamine 123, rhodamine X, sulforhodamine B, sulforhodamine 101, sulfonyl chloride derivative of sulforhodamine 101, tetramethyl rhodamine, riboflavin, rosolic acid, and terbium chelate derivatives).

Other detectable labels include an electron spin resonance molecule (such as for example nitroxyl radicals), a chemiluminescent molecule (e.g., chemiluminescent substrates), a radioisotope (e.g., P32 or H3, 14C, 125I and 131I), an optical or electron density marker, an enzyme, an enzyme substrate, a biotin molecule, a streptavidin molecule, an electrical charge transferring molecule (i.e., an electrical charge transducing molecule), a chromogenic substrate, a semiconductor nanocrystal, a semiconductor nanoparticle (such as quantum dots described for example in U.S. Pat. No. 6,207,392 and commercially available from Quantum Dot Corporation and Evident Technologies), a colloid gold nanocrystal, a ligand, a microbead, a magnetic bead, a paramagnetic particle, a quantum dot, an affinity molecule, a protein, a peptide, nucleic acid, a carbohydrate, an antigen, a hapten, an antibody, an antibody fragment, and a lipid. They are not so limited however.

REFERENCES

Berge, T., N. S. Jenkins, et al. (2002). "Structural perturbations in DNA caused by bis-intercalation of ditercalinium visualised by atomic force microscopy." *Nucleic Acids Res* 30(13): 2980-6.

Carlsson, C., M. Jonsson, et al. (1995). "Double bands in DNA gel electrophoresis caused by bis-intercalating dyes." *Nucleic Acids Research* 23(13): 2413-2420.

Carlsson, C., A. Larsson, et al. (1994). "Optical and Photophysical Properties of the Oxazole Yellow DNA Probes YO and YOYO." *The Journal of Physical Chemistry* 98(40): 10313-10321.

Chan, E. Y., N. M. Goncalves, et al. (2004). "DNA mapping using microfluidic stretching and single-molecule detection of fluorescent site-specific tags." *Genome Research* 14(6): 1137-1146.

Furstenberg, A., T. G. Deligeorgiev, et al. (2007). "Structure-fluorescence contrast relationship in cyanine DNA intercalators: Toward rational dye design." *Chem. Eur. J.* 13: 8600-8609.

Gunther, K., M. Mertig, et al. "Mechanical and structural properties of YOYO-1 complexed DNA." *Nucleic Acids Res* 38(19): 6526-32.

Jung, B., R. Bharadwaj, et al. (2006). "On-chip millionfold sample stacking using transient isotachophoresis." *Anal Chem* 78(7): 2319-27.

Krylova, S. M., V. Okhonin, et al. (2009). "Transverse diffusion of laminar flow profiles—a generic method for mixing reactants in capillary microreactor." *J Sep Sci* 32(5-6): 742-56.

Larson, J. W., G. R. Yantz, et al. (2006). "Single DNA Molecule Stretching in Sudden Mixed Shear and Elongational Microflows." *Lab on a Chip* 6: 1187-1199.

Larsson, A., C. Carlsson, et al. (1994). "Characterization of the Binding of the Fluorescent Dyes YO and YOYO to DNA by Polarized Light Spectroscopy." *Journal of the American Chemical Society* 116(19): 8459-8465.

Protozanova, E., M. Zhang, et al. (2010). "Fast high-resolution mapping of long fragments of genomic DNA based on single molecule detection." *Analytical Biochemistry*, 2010. 402: p. 83-90.

Shackman, J. G. and D. Ross (2007). "Gradient elution isotachophoresis for enrichment and separation of biomolecules." *Anal Chem* 79(17): 6641-9.

EXAMPLES

Example 1

On-Chip Intercalation with Mono-Cyanine Intercalator

This Examples demonstrates labeling of DNA using the mono-cyanine intercalator PO—PRO-1.

Off-chip ("bulk") fluorescence binding assays were performed in a reaction vessel. These assays suggested that the intercalation reaction approached saturation near 250 nM Po-PRO-1 in the presence of 50 nM DNA base pairs. At concentrations above 1 uM, the observed fluorescence intensity appeared to decrease, either due to aggregation of intercalator that in turn induced autoquenching of the fluorescent signal or due to aggregation and precipitation of the intercalated DNA.

Preliminary on-chip intercalation was then performed using 250 nM PO-PRO-1 in low ionic strength Tris-EDTA buffer. Initial microscopic observation indicated the presence of a single stream of intercalated DNA emerging from the DNA injection channel. No aggregation or surface adhesion was observed (FIG. 2). Use of the mono-intercalating dye promoted successful on-chip intercalation by eliminating DNA inter-molecular cross-linking and DNA adhesion to the chip surface(s). The off rate of PO-PRO is so high that if a DNA sample was intercalated in tube at 1:1 dye-intercalator ratio, no observable fluorescence is observable in the detection channel due to diffusion of the intercalator away from the DNA (data not shown).

Example 2

On-Chip Intercalation is Independent of DNA Concentration

Figure 3:
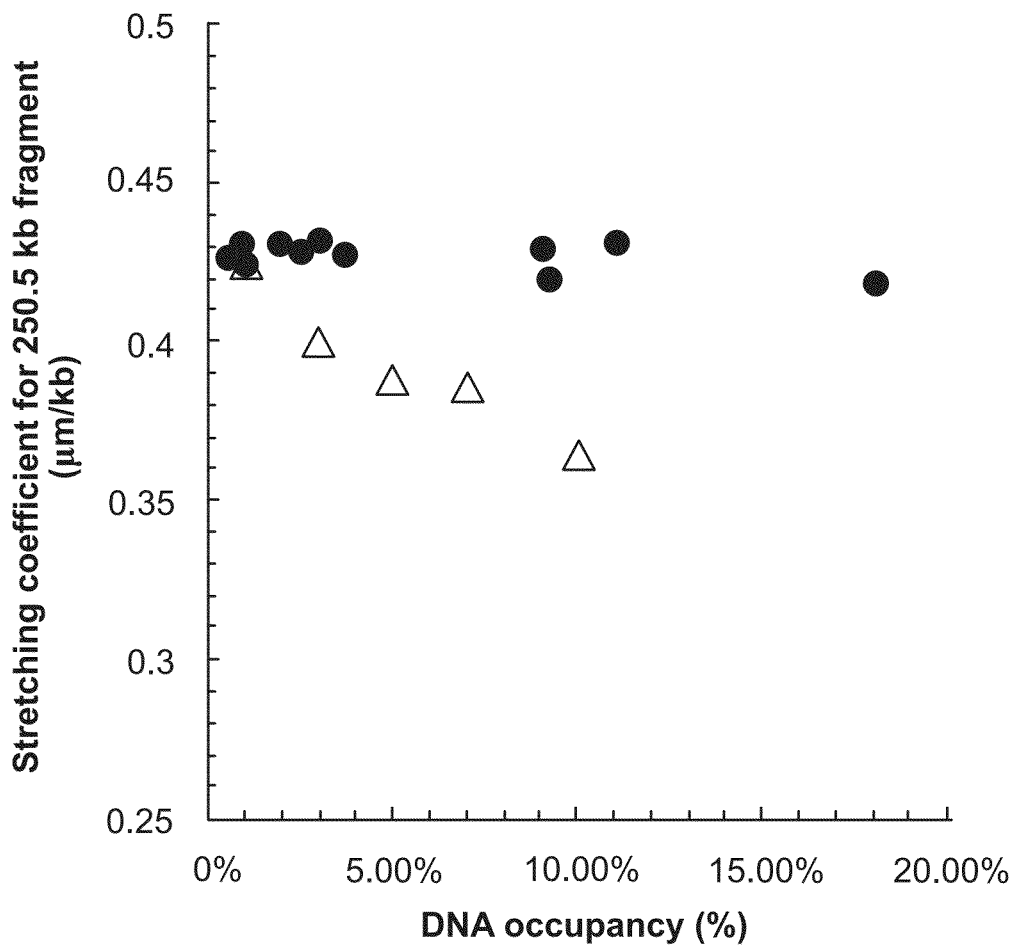
FIG. 3. On-chip intercalation of DNA spanning 32-fold serial concentration dilutions using PO-PRO-1 in sheath buffers (250 nM) results in uniform DNA stretching (closed circle). In-tube intercalation of DNA spanning only 7 fold concentration dilution, however, exhibits significant effect on DNA stretching, using fixed intercalator concentration (1 μM, open triangles).

For in-tube intercalation, solutions of varying DNA concentrations were incubated in a tube with a fixed concentration of the bis intercalator POPO-1 (1 μM POPO-1). The DNA was then introduced into a microfluidic device described herein. Each solution was introduced into the reaction chamber from which the DNA entered the elongation region (or elongation funnel), and 30 minute data sets were acquired. The stretching coefficient for the 250.5 kb fragment was determined as a representative value for each data set. We observed that the stretching coefficient decreased as the ratio of DNA to intercalator increased (FIG. 3, open triangles). Only a limited range of DNA to intercalator ratios were achieved, since at low dilutions of DNA, the frequency of molecules reaching the detector dropped precipitously (corresponding to the observed onset of fluorescence quenching and precipitation).

For on-chip intercalation, similar DNA solutions (of differing concentrations) were loaded to the type of microfluidic chip operating with 250 nM PO-PRO-1 in the sheathing buffer streams. In contrast to the in-tube intercalation, a uniform stretching coefficient was observed across a 32 fold dilution of the original stock DNA, when on-chip intercalation was used. (FIG. 3, closed circles)

Example 3

On-Chip Intercalation is Independent of Intercalator Concentration

This Example describes experiments performed to determine optimal conditions for intercalation by varying the concentration of intercalator in the sheathing buffer. A sample of E. coli K12 DNA digested with the NotI restriction enzyme was loaded to the injection port, and intercalator ranging from 50-500 nM was loaded with the sheathing buffer streams. Samples with no intercalator have been run on the instrument, but it is impossible to determine observed molecule lengths in the absence of intercalating dye. For each condition, fragment lengths (in μm) were determined for all restriction fragments by identifying each clustered fragment by its signature trace of site-specific probes. (Protozanova et al., Analytical Biochemistry, 2010. 402: p. 83-90.) When the measured fragment length (in μm) was plotted against the known fragment length in kb, characteristic quadratic stretching curves were observed (FIG. 4A). The extensibility of DNA increased with increasing PO-PRO-1 concentration.

Other Embodiments

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for uniformly labeling a nucleic acid with an intercalator comprising providing a capillary coupled to a microfluidic device, wherein the capillary comprises an intercalator, placing a first end of the capillary in a vessel comprising a nucleic acid, applying hydrodynamic or electrokinetic force sufficient to move the nucleic acid from the vessel through the capillary and to the microfluidic device, wherein flow of nucleic acid through the capillary is laminar, and wherein the intercalator is a mono intercalator, and wherein the capillary has dimensions of about 15 cm in length and about 150 micron internal diameter.

2. A method for uniformly labeling a nucleic acid with an intercalator comprising providing a microfluidic device comprising a sample inlet, a sheath fluid inlet, an elongation region, and a waste reservoir downstream of the elongation region, introducing a nucleic acid into the microfluidic device through the sample inlet, introducing intercalator into the microfluidic device through the sheath fluid inlet, and applying hydrodynamic force sufficient to move the nucleic acid from the sample inlet and the intercalator from the sheath fluid inlet through the elongation region to the waste reservoir, wherein flow of the nucleic acid and intercalator is laminar, and wherein the intercalator is a mono intercalator.

3. The method of claim 2, wherein the intercalator is in a buffered solution.

4. The method of claim 3, wherein the buffered solution includes Tris-EDTA buffer.

5. The method of claim 2, wherein the intercalator is a mono-cyanine intercalator.

6. The method of claim 2, wherein the intercalator is PO-PRO-1.

7. The method of claim 2, wherein the intercalator is PO-PRO-3.

8. The method of claim 2, wherein the microfluidic device is coated with an electroosmotic flow (EOF) suppressor on one or more of its interior surfaces.

9. The method of claim 2, wherein intercalator is flowed through and is present in the microfluidic device prior to introduction of the nucleic acid.

10. The method of claim 2, wherein the microfluidic device comprises two sheath fluid inlets positioned on opposite sides of the sample inlet, and intercalator is introduced into the microfluidic device through both sheath fluid inlets.

11. The method of claim 2, wherein nucleic acids are exposed to intercalator individually.

12. The method of claim 2, wherein nucleic acids are exposed to the intercalator while under tension.

13. The method of claim 2, wherein the intercalator is present at a concentration ranging from 1 µM to less than 10 µM.

14. A microfluidic device comprising a sample inlet port, a sheath inlet port, an elongation region, and a waste reservoir downstream of the elongation region, wherein the sheath inlet port and the elongation region comprise a nucleic acid intercalator prior to introduction of a nucleic acid sample, wherein the intercalator is a mono intercalator.

15. The microfluidic device of claim 14, further comprising a microfluidic channel having a depth of 2 microns.

16. The microfluidic device of claim 14, wherein the elongation region comprises a first zone and a second zone, wherein the first zone has a first tapered shape and the second zone has a second tapered shape different from the first tapered shape.

17. The microfluidic device of claim 16, wherein the elongation region comprises a first zone and a second zone, wherein the first zone has a first tapered shape and the second zone has a second tapered shape different from the first tapered shape.

18. A method for uniformly labeling a nucleic acid with an intercalator comprising providing a microfluidic chip comprising a sample inlet, an intercalator inlet, two sheath fluid inlets, an elongation region, and a waste reservoir downstream of the elongation region, wherein two intercalator channels extend from the intercalator inlet and merge with a sample channel extending from the sample inlet, and wherein the intercalator channels are positioned on opposite sides of the sample channel and the two sheath fluid inlets are positioned on opposite sides of, and feed into, the elongation region, introducing a nucleic acid into the microfluidic chip through the sample inlet, introducing intercalator into the microfluidic chip through the intercalator inlet, and applying hydrodynamic force sufficient to move the nucleic acid from the sample inlet and the intercalator from the intercalator inlet through the elongation region to the waste reservoir, wherein flow of the nucleic acid and intercalator is laminar, and wherein the intercalator is a mono intercalator.

19. A microfluidic device comprising a sample inlet, a sample channel extending from the sample inlet, an intercalator inlet, two intercalator channels extending from the intercalator inlet and merging with the sample channel, the two intercalator channels being positioned on opposite sides of the sample channel, an elongation region, two sheath fluid inlets that are positioned on opposite sides of, and feed into, the elongation region, and a waste reservoir downstream of the elongation region, wherein the intercalator inlet and the elongation region comprise a nucleic acid intercalator prior to introduction of a nucleic acid sample.

20. The microfluidic device of claim 19, wherein the two intercalator channels and the sample channel merge to form an intercalation reaction channel that comprises a microfluidic channel having a depth of 2 microns.

21. The microfluidic device of claim 19, wherein the nucleic acid intercalator is a mono intercalator.

* * * * *